(12) United States Patent
Mustapha

(10) Patent No.: US 11,920,926 B2
(45) Date of Patent: Mar. 5, 2024

(54) MEASURING DEVICE AND A MEASUREMENT METHOD THEREOF

(71) Applicant: Jihad Ali Mustapha, Ada, MI (US)

(72) Inventor: Jihad Ali Mustapha, Ada, MI (US)

( * ) Notice: Subject to any disclaimer, the term of this patent is extended or adjusted under 35 U.S.C. 154(b) by 0 days.

(21) Appl. No.: 17/746,694

(22) Filed: May 17, 2022

(65) Prior Publication Data

US 2022/0364841 A1 Nov. 17, 2022

Related U.S. Application Data

(60) Provisional application No. 63/189,558, filed on May 17, 2021.

(51) Int. Cl.
*G01B 5/08* (2006.01)
*G01B 5/00* (2006.01)

(52) U.S. Cl.
CPC ............ *G01B 5/08* (2013.01); *G01B 5/0004* (2013.01)

(58) Field of Classification Search
USPC .......................... 33/1 BB, 485, 759, 511, 512
See application file for complete search history.

(56) References Cited

U.S. PATENT DOCUMENTS

| | | | | |
|---|---|---|---|---|
| 778,659 A * | 12/1904 | Guth | ................... | G01B 3/06 33/463 |
| 1,170,174 A * | 2/1916 | Matson | .................... | B43L 9/04 33/485 |
| 2,932,296 A * | 4/1960 | Sanders | ................. | A61B 17/32 606/167 |
| 4,279,259 A * | 7/1981 | Lee | .......................... | A41H 1/02 600/587 |
| 4,974,331 A * | 12/1990 | Watterson | ................ | A41H 1/02 33/15 |
| 5,619,804 A | 4/1997 | Vogt et al. | | |
| 5,814,098 A * | 9/1998 | Hinnenkamp | ........ | A61F 2/2496 600/587 |
| 6,097,978 A * | 8/2000 | Demarais | .................. | A61F 2/07 378/205 |
| 6,276,069 B1 * | 8/2001 | Chadwick | ................ | A41H 1/02 235/78 R |
| 9,516,993 B2 * | 12/2016 | Ito | ........................ | A61B 5/7246 |
| 9,668,656 B2 | 6/2017 | Banet et al. | | |

(Continued)

FOREIGN PATENT DOCUMENTS

| | | | |
|---|---|---|---|
| CN | 105547097 A | * | 5/2016 |
| CN | 108032652 A | * | 5/2018 |
| WO | WO-2020160674 A1 | * | 8/2020 |

OTHER PUBLICATIONS

International Search Report and Written Opinion dated Sep. 6, 2022, directed to International Patent Application No. PCT/US2022/029660; 7 pages.

*Primary Examiner* — Christopher W Fulton
(74) *Attorney, Agent, or Firm* — Michele V. Frank; Venable LLP

(57) ABSTRACT

A measurement device and method that allows for precise placement, as well as more accurate measurement of various body parts, including vessels, lesions, and/or lumens of vessels of various body parts. The measurement device comprises one or more measurement tapes having (i) a plurality of measurement marks for measuring a distance and/or a length of a vessel and (ii) a plurality of circular indicators for measuring a diameter of a lumen of the vessel.

34 Claims, 19 Drawing Sheets

(56) References Cited

U.S. PATENT DOCUMENTS

| | | | |
|---|---|---|---|
| 9,671,209 B2* | 6/2017 | O'Hara | G01B 5/12 |
| 10,441,304 B2* | 10/2019 | Deister | A61B 17/282 |
| 11,525,659 B2* | 12/2022 | Crockett | B25H 7/00 |
| 2015/0089824 A1* | 4/2015 | Moore | A61B 5/4312 |
| | | | 33/512 |
| 2015/0216613 A1* | 8/2015 | Schilling | A61B 5/6841 |
| | | | 33/512 |
| 2016/0113549 A1 | 4/2016 | Harfouche | |
| 2017/0275880 A1 | 9/2017 | Vanker et al. | |
| 2019/0045768 A1* | 2/2019 | Rasmussen | G01G 19/60 |

\* cited by examiner

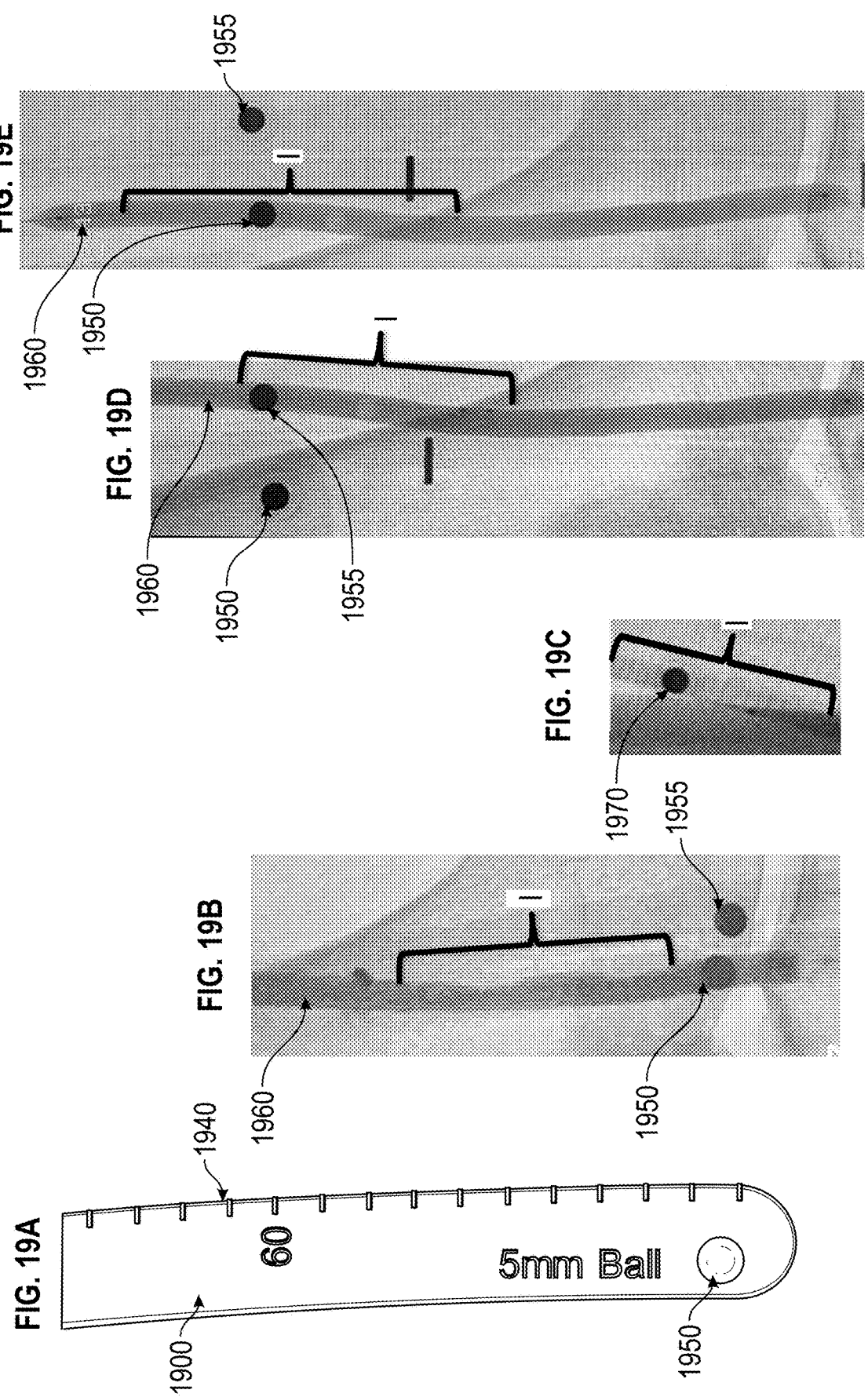

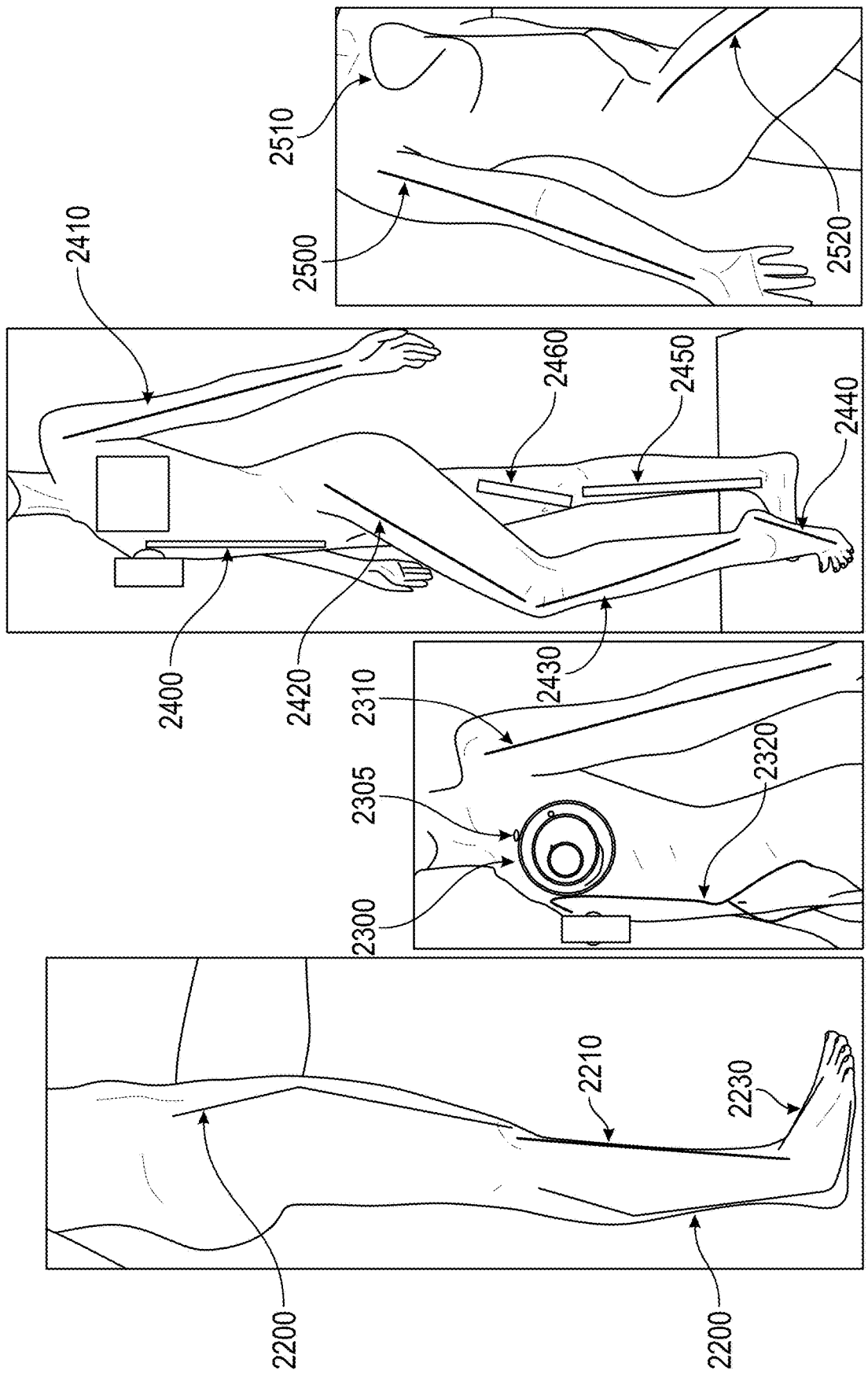

MEASURING DEVICE AND A MEASUREMENT METHOD THEREOF

RELATED APPLICATION

This application claims the priority of U.S. provisional application No. 63/189,558, filed May 17, 2021, which is incorporated herein by reference in its entirety for all purposes.

TECHNICAL FIELD

The present invention relates to a measuring device and a measurement method for measuring body parts, including, e.g., vessels and/or lesions of vessels.

BACKGROUND

Current devices and methods for measuring body parts, including, e.g., vessels and/or lesions of vessels, for various surgical procedures allow for measuring only a single distance between two points of reference. These measuring devices and methods do not generally allow for measurements that capture anterior plus posterior views and/or oblique views for certain body parts that may be necessary for various surgical procedures.

BRIEF SUMMARY OF THE INVENTION

According to one embodiment, the present invention provides a measuring device comprising one or more measurement tapes having (i) a plurality of measurement marks for measuring one or more of a distance and a length of a vessel and (ii) a plurality of circular indicators for measuring a diameter of a lumen of the vessel.

According to an embodiment, each measurement mark of the plurality of measurement marks is positioned the same distance from an adjacent measurement mark of the plurality of measurement marks. According to an embodiment, each measurement mark of the plurality of measurement marks is positioned 5 centimeters from an adjacent measurement mark of the plurality of measurement marks. According to an embodiment, each measurement mark of the plurality of measurement marks is positioned 1 centimeter from an adjacent measurement mark of the plurality of measurement marks.

According to an embodiment, each measurement mark of the plurality of measurement marks comprises a number.

According to an embodiment, a plurality of sub-markers is positioned between each measurement mark of the plurality of measurement marks. According to an embodiment, each sub-marker of the plurality of sub-markers is positioned the same distance from an adjacent sub-marker of the plurality of sub-markers. According to an embodiment, each sub-marker of the plurality of sub-markers is positioned 1 centimeter from an adjacent sub-marker of the plurality of sub-markers.

According to one embodiment, the measuring device comprises at least two measurement tapes that comprise mirror images of each other. According to one embodiment, the measuring device comprises at least two measurement tapes that are positioned parallel to each other. According to one embodiment, the measuring device comprises at least two measurement tapes that are connected via one or more straps. According to one embodiment, the one or more straps further comprise a plurality of measurement marks.

According to one embodiment, the measuring device comprises at least two measurement tapes in the form of a y-shape with (i) the at least two measurement tapes being positioned parallel to each other along a first length, and (ii) the at least two measurement tapes diverging at an angle with respect to each other along a second length to form the y-shape.

According to an embodiment, the measuring device comprises at least one measurement tape having (i) a first portion that is straight and (ii) a second portion that is at an angle relative to the first portion. According to an embodiment, the measuring device further includes an indicator portion that is configured to enhance an angulation of the measuring device.

According to an embodiment, the measuring device comprises at least one measurement tape that is 70 cm in length.

According to an embodiment, the plurality of circular indicators for measuring a diameter of a lumen are differing sizes from each other. According to one embodiment, the plurality of circular indicators comprise differing sizes that include two or more of (i) a 2 mm diameter circle, (ii) a 2.5 mm diameter circle, (iii) a 3 mm diameter circle, (iv) a 3.5 mm diameter circle, (v) a 4 mm diameter circle, (vi) a 5 mm diameter circle, (vii) a 5.5 mm diameter circle, (viii) a 6 mm diameter circle, (ix) a 6.5 mm diameter circle, (x) a 7 mm diameter circle, and (xi) an 8 mm diameter circle.

According to an embodiment, the plurality of circular indicators for measuring a diameter of a lumen comprise radiopaque markers.

According to another embodiment, the present invention provides a method of measuring at least one of (i) one or more of a distance and a length of a vessel and (ii) a diameter of a lumen of a vessel. The method includes (a) providing a measuring device comprising one or more measurement tapes having (i) a plurality of measurement marks for measuring the one or more of a distance and a length of the vessel and (ii) a plurality of circular indicators for measuring the diameter of the lumen of the vessel; (b) positioning the measuring device on a body part of a patient, and (c) measuring the at least one of (i) one or more of a distance and a length of the vessel and (ii) a diameter of a lumen of the vessel.

According to one embodiment, the measuring device comprises at least one measurement tape, and the method includes positioning the at least one measurement tape along a thigh of a patient to measure a vessel within the thigh of the patient.

According to one embodiment, the measuring device comprises at least two measurement tapes, and the method includes positioning (i) a first measurement tape of the at least two measurement tapes along a calf of a patient, and (ii) a second measurement tape of the at least two measurement tapes along a shin of a patient. According to another embodiment, the method further includes positioning (i) a portion of the first measurement tape of the at least two measurement tapes along a bottom or plantar portion of a foot of the patient, and (ii) a portion of the second measurement tape of the at least two measurement tapes along a top or dorsal portion of the foot of the patient.

According to another embodiment, the present invention provides a measuring device comprising at least one measurement tape having (i) a plurality of measurement marks for measuring one or more of a distance and a length of a vessel and (ii) a plurality of cylindrical elements that each house a measuring sphere for measuring a diameter of a lumen of the vessel.

According to another embodiment, the present invention provides a measuring device comprising at least one measurement tape having at least one measuring sphere, wherein the at least one measuring sphere comprises a radiopaque material that allows for visualizing the at least one measuring sphere under x-ray at any angle.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIGS. 19A-19E are photographs that illustrate a method of using a measuring device having at least one measuring sphere to achieve an equivalent diameter between the sphere and an inflatable balloon inserted into a vessel of a patient according to an embodiment of the invention.

FIGS. 22A-22D are photographs that depict various measuring devices that can be placed on various body parts of a human patient according to embodiments of the invention.

DETAILED DESCRIPTION OF THE INVENTION

Figure 1:
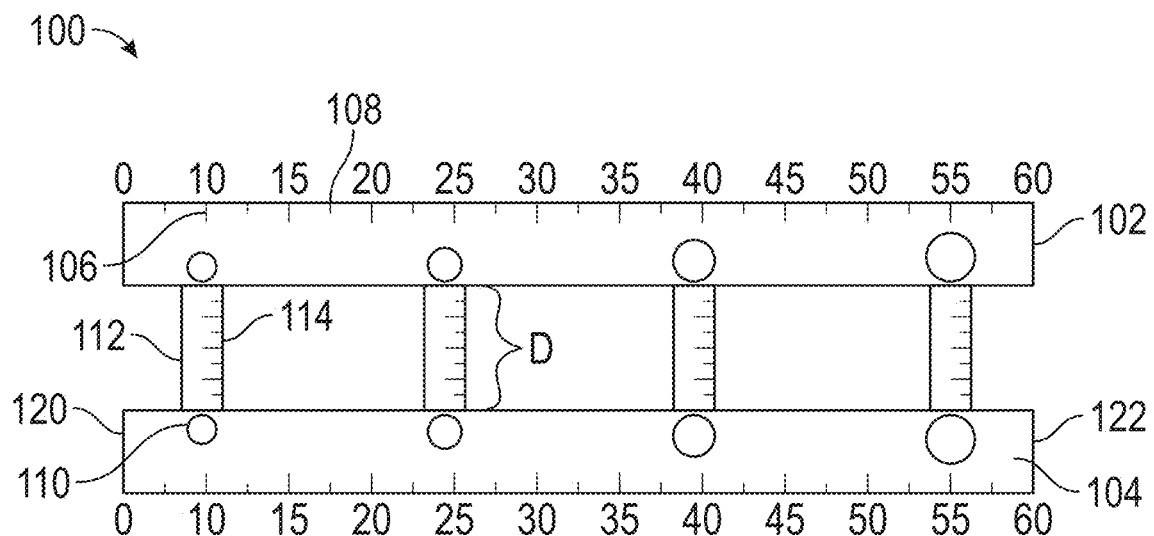
FIG. 1 is an illustration of a measuring device according to one embodiment of the invention.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though they may. Furthermore, the phrases "in another embodiment" and "in some other embodiments" as used herein do not necessarily refer to a different embodiment, although they may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, terms such as "comprising," "including," and "having" do not limit the scope of a specific claim to the materials or steps recited by the claim.

As used herein, the terms "measuring tape" or "measurement tape" refer to a strip of material that is marked with units (including, e.g., inches, centimeters, millimeters, etc.) for measuring things.

Although the terms "circular" or "sphere" or "ball" are used herein for a shape to measure, e.g., a diameter, the shape of this indicator is not limited to only these shapes and encompasses any shape that is capable of being viewed from multiple angles, including under, e.g., x-ray.

The present invention relates to a measuring device and a measurement method for measuring body parts, including, e.g., vessels, lumens, lesions of vessels, masses, balloons inserted into vessels, etc., as well as any portion of the vascular system and anywhere in the body where arteries and/or veins are provided. There is a need for an improved measurement device and method that allows for precise placement, as well as more accurate measurement of various body parts. There is also a need for an improved measurement device that is both rigid and flexible, while avoiding the foreshortening of previously known measurement devices. The present invention relates to a measuring device and a measurement method that comprises one or more measurement tapes having (i) a plurality of measurement marks for measuring a distance and/or a length of a vessel and (ii) a plurality of circular indicators for measuring a diameter of, e.g., a lumen of the vessel.

The present invention relates to a measuring device and a measurement method. According to one embodiment, the measuring device comprises one or more measurement tapes having (i) a plurality of measurement marks for measuring a distance and/or a length of a vessel and (ii) a plurality of circular indicators for measuring a diameter of a lumen of the vessel. This unique combination of measuring the length of a vessel (including, e.g., a length of a lesion, lumen, and/or mass of the vessel) along with providing a reference diameter of a lumen and/or mass of the vessel helps in the treatment of vessels that are not associated with any other reference catheters or structures, which render them undersized or oversized for treatment. This uniquely combined measuring tool that has a means for circumferential measuring as well as a means for longitudinal measuring allows for a quick assessment of a vessel and/or a lesion length and diameter for operators to provide the appropriate diameter size and treatment length tool (such as, e.g., an inflatable balloon for balloon angioplasty).

Figure 2:
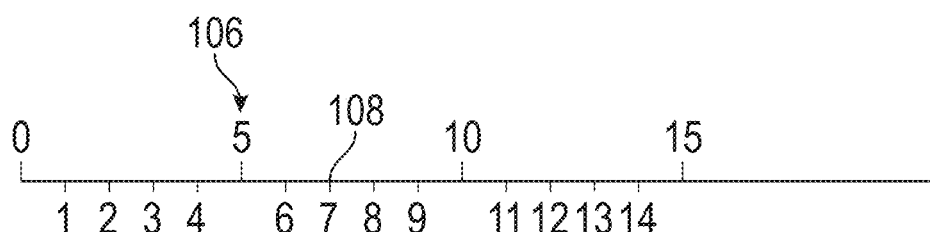
FIG. 2 is an illustration of a plurality of measurement marks according to an embodiment of the invention.

For example, as shown in the embodiment of FIG. 1, the measuring device 100 comprises a first measuring tape 102 and a second measuring tape 104 that are positioned in parallel to each other. Each of the measuring tapes 102, 104 includes a plurality of measurement marks 106 and a plurality of sub-markers 108 for measuring a distance and/or a length of, for example, a vessel. Each of the measurement marks 106 is positioned the same distance from an adjacent measurement mark 106. According to an embodiment, each measurement mark 106 is positioned 5 centimeters from an adjacent measurement mark 106. According to an embodiment, each measurement mark 106 is positioned 1 centimeter from an adjacent measurement mark 106. Each of the sub-markers 108 is positioned the same distance from an adjacent sub-marker 108. According to an embodiment, each sub-marker 108 is positioned 1 centimeter from an adjacent sub-marker 108. For example, as shown in the embodiment of FIG. 2, each measurement mark 106 is positioned 5 centimeters from an adjacent measurement mark 106, while each sub-marker 108 is positioned 1 centimeter from an adjacent sub-marker 108. According to an embodiment, each measurement mark of the plurality of measurement marks comprises a number (see, e.g., FIG. 2).

As further shown in FIG. 1, each of the measuring tapes 102, 104 further includes a plurality of circular indicators 110 for measuring a diameter of, for example, a lumen of a vessel. As shown in the embodiment of FIG. 1, the plurality of circular indicators 110 are differing sizes from each other, with the circular indicators 110 increasing in size from a left side to a right side of the device 100. According to an embodiment, the plurality of circular indicators 110 for measuring the diameters and/or lumens comprise radiopaque markers. According to one embodiment, the circular indicators 110 on the left side of the measuring tapes 102, 104 are the smallest in size and are spherical in shape.

The plurality of circular indicators 110 can be filled with a radiopaque solution that is not affected or impacted by placing the measuring device 100 on the body, and, thus, a spherical diameter of the circular indicators 110 will always be maintained at the intended initial diameter. For example, according to one embodiment, the circular indicator 110 at a distal end 120 (or left side) of each of the measuring tapes 102, 104 will be 2 mm in diameter, with the diameter of each of the circular indicators 110 increasing in size by 1 mm from the distal end 120 to a proximal end 122 (or left side to right side) of each of the measuring tapes 102, 104.

As shown in the embodiment of FIG. 1, the first measuring tape 102 is a mirror image of the second measuring tape 104. According to one embodiment, the first measuring tape 102 is a mirror image and/or parallel to the second measuring tape 104 to allow for the measuring device 100 to be used in positions such as, e.g., anterior and medial, posterior and lateral, and any other combination where multiple views are needed and hence, the ability to maintain visualization of the location of a vessel and/or a lesion of the vessel is needed with certain accuracy (see, e.g., FIG. 6).

As further shown in FIG. 1, the first measuring tape 102 is attached to the second measuring tape 104 via one or more straps 112. By including the one or more straps 112, a distance (D) between the first and second measuring tapes 102, 104 can be maintained, which allows for an operator to visualize a vessel and/or a lesion length regardless of whether an oblique view is being used. According to one embodiment, the first measuring tape 102 is loosely attached or connected to the second measuring tape 104 via the one or more straps 112. According to one embodiment, the connection of the first measuring tape 102 to the second measuring tape 104, via the one or more straps 112, maintains a constant distance (D) between the first and second measuring tapes 102, 104. Each of the straps 112 further includes a plurality of measurement marks 114. By including the measurement marks 114 on the straps 112, a distance (D) between the first and second measuring tapes 102, 104 can be determined, which also can be used to measure a circumference of a target body part (e.g., a calf area), if necessary.

Figure 3:
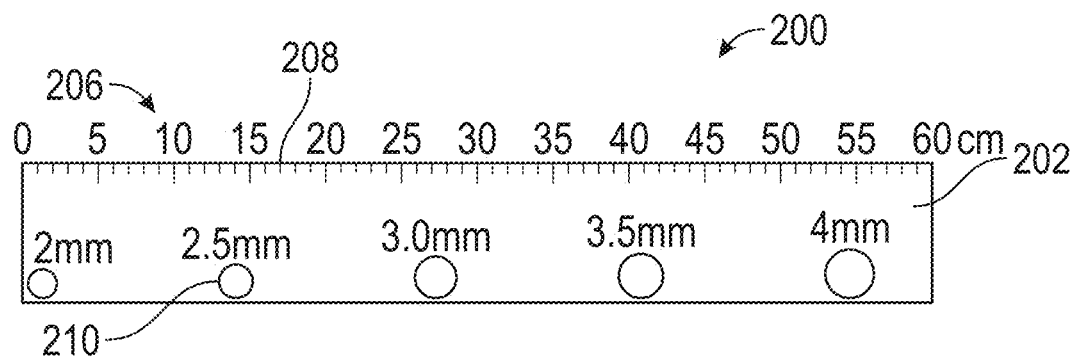
FIG. 3 is an illustration of a measuring device according to one embodiment of the invention.

FIG. 3 illustrates an embodiment of a measuring device 200 that comprises a single measuring tape 202 having a plurality of measurement marks 206 and a plurality of sub-markers 208 for measuring a distance and/or a length of, for example, a vessel. Each of the measurement marks 206 is positioned the same distance from an adjacent measurement mark 206. According to one embodiment, each of the measurement marks 206 is positioned 1 centimeter from an adjacent measurement mark 206, while each of the sub-markers 208 is positioned 0.5 centimeters from an adjacent sub-marker 208.

As further shown in FIG. 3, the single measuring tape 202 further includes a plurality of circular indicators 210 for measuring a diameter of, for example, a lumen of a vessel. As shown in the embodiment of FIG. 3, the plurality of circular indicators 210 are differing sizes from each other, with the circular indicators 210 increasing in size from a left side to a right side of the device 200. For example, as shown in the embodiment of FIG. 3, the first circular indicator 210 positioned at the left side of the measuring tape 202 is 2 mm in diameter, the second circular indicator 210 is 2.5 mm in diameter, the third circular indicator 210 near the mid-point of the measuring tape 202 is 3.0 mm in diameter, the fourth circular indicator 210 is 3.5 mm in diameter, and the fifth circular indicator 210 positioned at the right side of the measuring tape 202 is 4 mm in diameter. According to an embodiment, the plurality of circular indicators 210 for measuring diameters and/or lumens comprise radiopaque markers.

Figure 4:
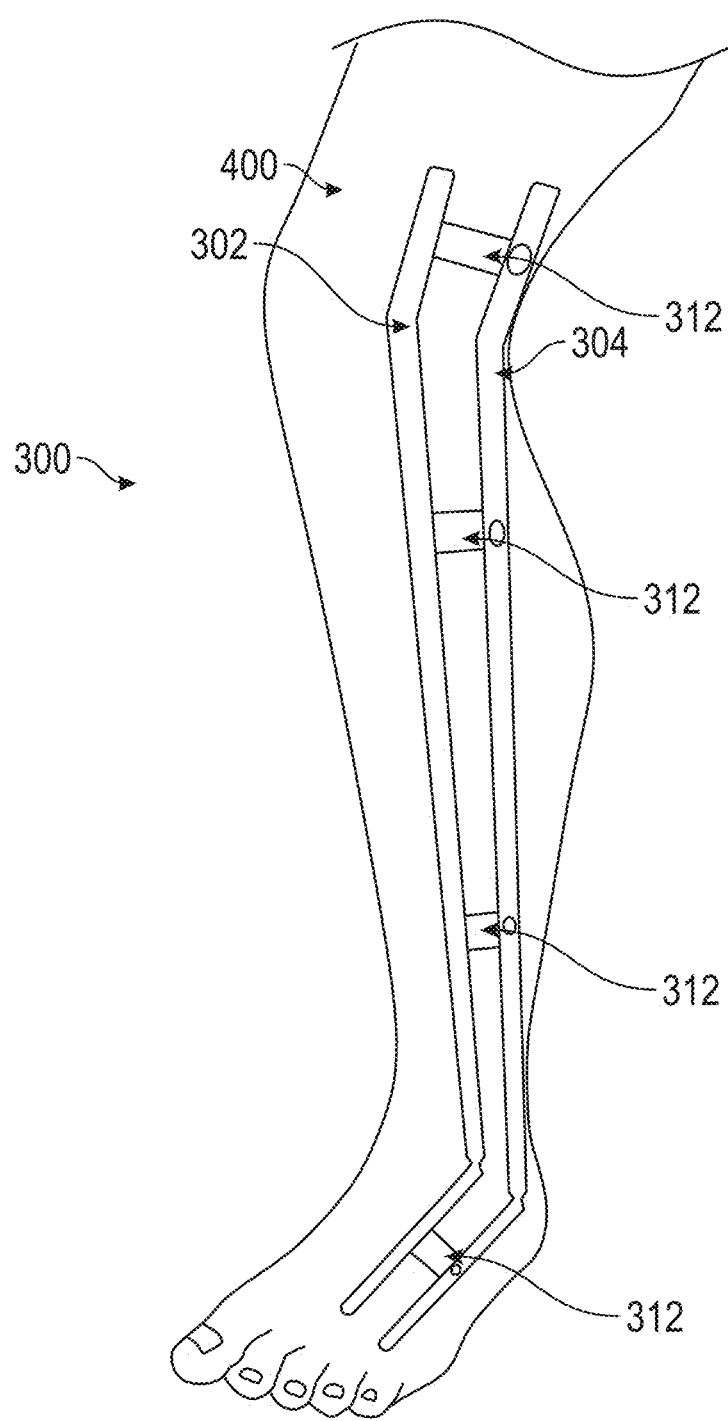
FIG. 4 is an illustration of a measuring device positioned along a calf and foot of a patient according to one embodiment of the invention.

FIG. 4 illustrates an embodiment of a measuring device 300 positioned along a leg 400 of a patient. In particular, as shown in the embodiment of FIG. 4, the measuring device 300 includes (i) a first measurement tape 302 that is positioned on the shin and a dorsal portion of a foot (i.e., a top of the foot) of the patient, and (ii) a second measurement tape 304 that is positioned on the calf and a plantar portion of a foot (i.e., a portion that is adjacent to the heel and/or the bottom of the foot) of the patient. As further shown in the embodiment of FIG. 4, the first measurement tape 302 extends above the knee of the patient to an area near the front of the thigh of the patient, and the second measurement tape 304 extends up the calf of the patient to an area near the back of the thigh of the patient. According to an embodiment, the first measurement tape 302 can be connected to the second measurement tape 304 via one or more straps 312. See also, e.g., the embodiment of FIG. 6, which is further discussed below.

Figure 5:
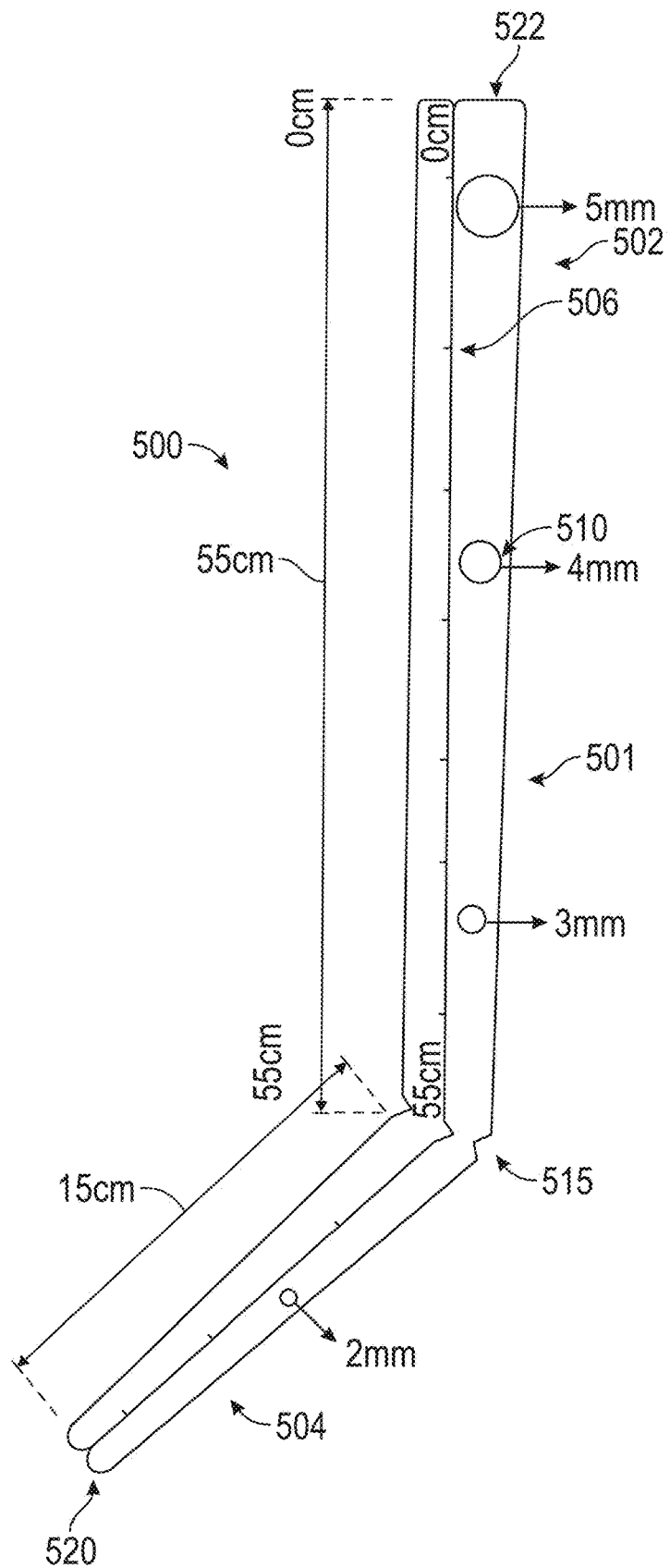
FIG. 5 is an illustration of a measuring device according to one embodiment of the invention.

FIG. 5 illustrates an embodiment of a measuring device 500 that comprises a single measuring tape 501 having a first portion 502 and a second portion 504. As shown in the embodiment of FIG. 5, the first portion 502 is straight, while the second portion 504 is at an angle relative to the first portion 502. According to one embodiment, the first portion 502 of the measuring device 500 is about 55 cm in length, while the second portion 504 of the measuring device 500 is about 15 cm in length. According to one embodiment, the measuring device 500 includes an indicator portion 515 that is configured to enhance an angulation of the measuring device 500. For example, the indicator portion 515 can be configured to enhance an angulation of the measuring device 500 between a foot of a patient (on which the second portion 504 of the measuring device 500 can be positioned) and an area above an ankle of a patient (on which the first portion 502 of the measuring device 500 can be positioned).

As further shown in FIG. 5, the measuring device 500 also includes (i) a plurality of measurement marks 506 for measuring a distance and/or a length of, for example, a vessel, and (ii) a plurality of circular indicators 510 for measuring a diameter of, for example, a lumen of a vessel. According to an embodiment, the plurality of circular indicators 510 differ in size. According to another embodiment, the plurality of circular indicators 510 increase in size from a distal end 520 to a proximal end 522 of the measuring device 500. For example, each circular indicator 510 of the plurality of circular indicators 510 can comprise one or more of (i) a 2 mm diameter circle, (ii) a 3 mm diameter circle, (iii) a 4 mm diameter circle, and (iv) a 5 mm diameter circle, with each circular indicator 510 increasing in size from the distal end 520 to the proximal end 522, such that a 2 mm diameter circle is positioned near the distal end 520 and a 5 mm diameter circle is positioned near the proximal end 522. According to one embodiment, the measuring device 500 of FIG. 5 can be positioned along the tibial femoral joint, which is the portion of the body where the femur meets the tibia (e.g., the measuring device 500 can be positioned along the foot of a patient and extend to an area at and/or above the knee of the patient).

Figure 6:
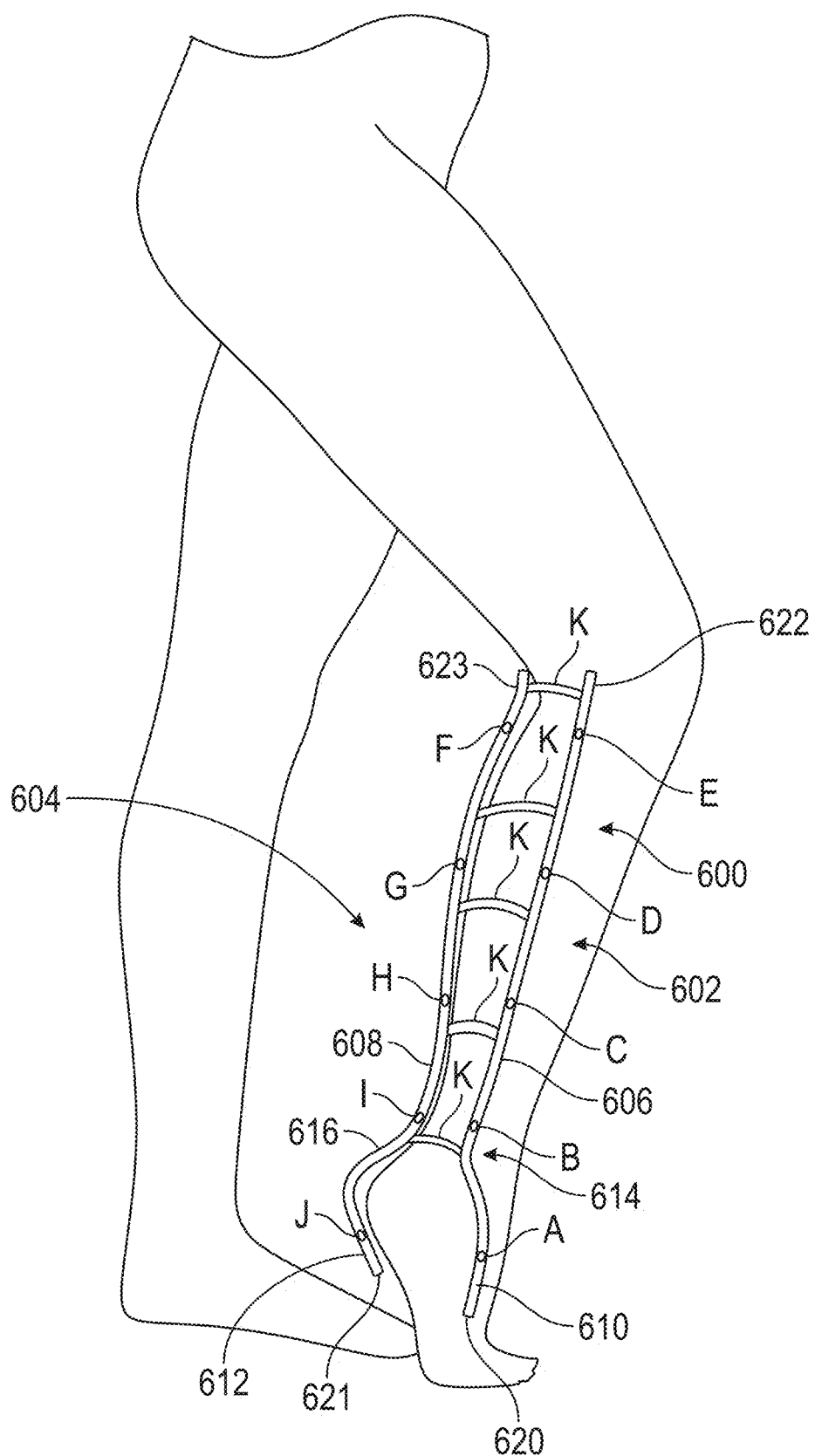
FIG. 6 is an illustration of a measuring device positioned along a calf, a shin, and a foot of a patient according to one embodiment of the invention.

According to another embodiment, a measuring device is provided that comprises at least one measurement tape that separates into the shape of a Y, which allows for the placement of the at least one measurement tape on, for example, (i) a plantar aspect/portion of a foot (i.e., the bottom of the foot), (ii) a dorsal portion of the foot (i.e., the top of the foot), and (iii) the back of a calf, the front of a calf and/or a shin of a patient. For example, as shown in the embodiment of FIG. 6, a measuring device 600 comprises a first measuring tape 602 and a second measuring tape 604 that are in the form of a Y-shape. The first measuring tape 602 includes a first portion 606 that is positioned substantially parallel to a first portion 608 of the second measuring tape 604. According to the embodiment of FIG. 6, the first portion 606 of the first measuring tape 602 is connected to the first portion 608 of the second measuring tape 604 via a plurality of straps (K). The first measuring tape 602 further includes a second portion 610 that is spaced apart from and/or diverges at an angle with respect to a second portion 612 of the second measuring tape 604. For example, as shown in the embodiment of FIG. 6, the first portion 606 of the first measuring tape 602 is substantially straight, while the second portion 610 of the first measuring tape 602 extends at an angle with respect to the first portion 606 (see, e.g., area 614). Similarly, the first portion 608 of the second measuring tape 604 is substantially straight, while the second portion 612 of the second measuring tape 604 extends at an angle with respect to the first portion 604 (see, e.g., area 616). Thus, as shown in the embodiment of FIG. 6, the configuration of the first and second portions 606, 610 of the first measuring tape 602 with respect to the first and second portions 608, 612 of the second measuring tape 604 creates or forms a y-shape. Moreover, as shown in the embodiment of FIG. 6, the first portion 606 of the first measuring tape 602 can be placed along the front of a calf and/or a shin of a patient, while (i) the first portion 608 of the second measuring tape 604 can be placed along the back of a calf, (ii) the second portion 610 of the first measuring tape 602 can be placed along the dorsal portion (or top) of a foot, and (iii) the second portion 612 of the second measuring tape 604 can be placed along the plantar portion (or bottom) of a foot.

As further shown in the embodiment of FIG. 6, each of the measuring tapes 602, 604 includes a plurality of circular indicators (A, B, C, D, E, F, G, H, I, J) for measuring a diameter of, for example, a lumen of a vessel. According to an embodiment, the plurality of circular indicators (A, B, C, D, E, F, G, H, I, J) for measuring the diameters and/or lumens comprise radiopaque markers and/or spheres. According to one embodiment, the plurality of circular indicators (A, B, C, D, E, F, G, H, I, J) differ in size and/or increase in size from a distal end 620, 621 to a proximal end 622, 623 of the first and second measuring tapes 602, 604, respectively. For example, according to one embodiment, the circular indicator A at the distal end 620 of the first measuring tape 602, as well as the circular indicator J at the distal end 621 of the second measuring tape 604, is 2 mm in diameter. The circular indicators thereafter (i.e., B, C, D, E, F, G, H, I) increase in size, with (i) the circular indicators B, I being 2.5 mm in diameter, (ii) the circular indicators C, H being 3 mm in diameter, (iii) the circular indicators D, G being 3.5 mm in diameter, and (iv) the circular indicators E, F, which are at the proximal ends 622, 623 of the first and second measuring tapes 602, 604, respectively, being 4 mm in diameter.

According to this configuration, the measuring device and/or the measurement tape(s) can be positioned on a foot of a patient on both a dorsal portion and a plantar portion of the foot simultaneously, which is especially helpful during complex procedures. Moreover, the circular indicators (A, B, C, D, E, F, G, H, I, J) or spherical correlation points, which are included, can be present both in the foot and calf areas, while also extending all the way to the groin area. This is a new, unique feature not provided in the past which now allows physicians to have a measuring tool that can measure the length and diameter of a vessel and/or a lesion despite the view chosen to use during the diagnostic and intervention procedures. Moreover, the Y-shaped measuring device, along with the circular indicators (or spheres) on the device, can allow for reference points of the media malleolus and the lateral malleolus of the foot and/or the ankle joint plus the knee joint and the hip joint as reference points to place the zero position (e.g., one end) of the measuring device and/or the measuring tape due to, for example, the variation in the length of the measuring tapes of the device. According to one embodiment, the measuring device 600 of the embodiment of FIG. 6 can comprise a dorsal tape, an anterior-lateral tape, and a plantar tape, which thus allows for the measuring device 600 to be positioned along the pedal loop and the tibial-pedal portion with a pair of parallel tapes (i.e., the first and second measuring tapes 602, 604).

Figure 7:
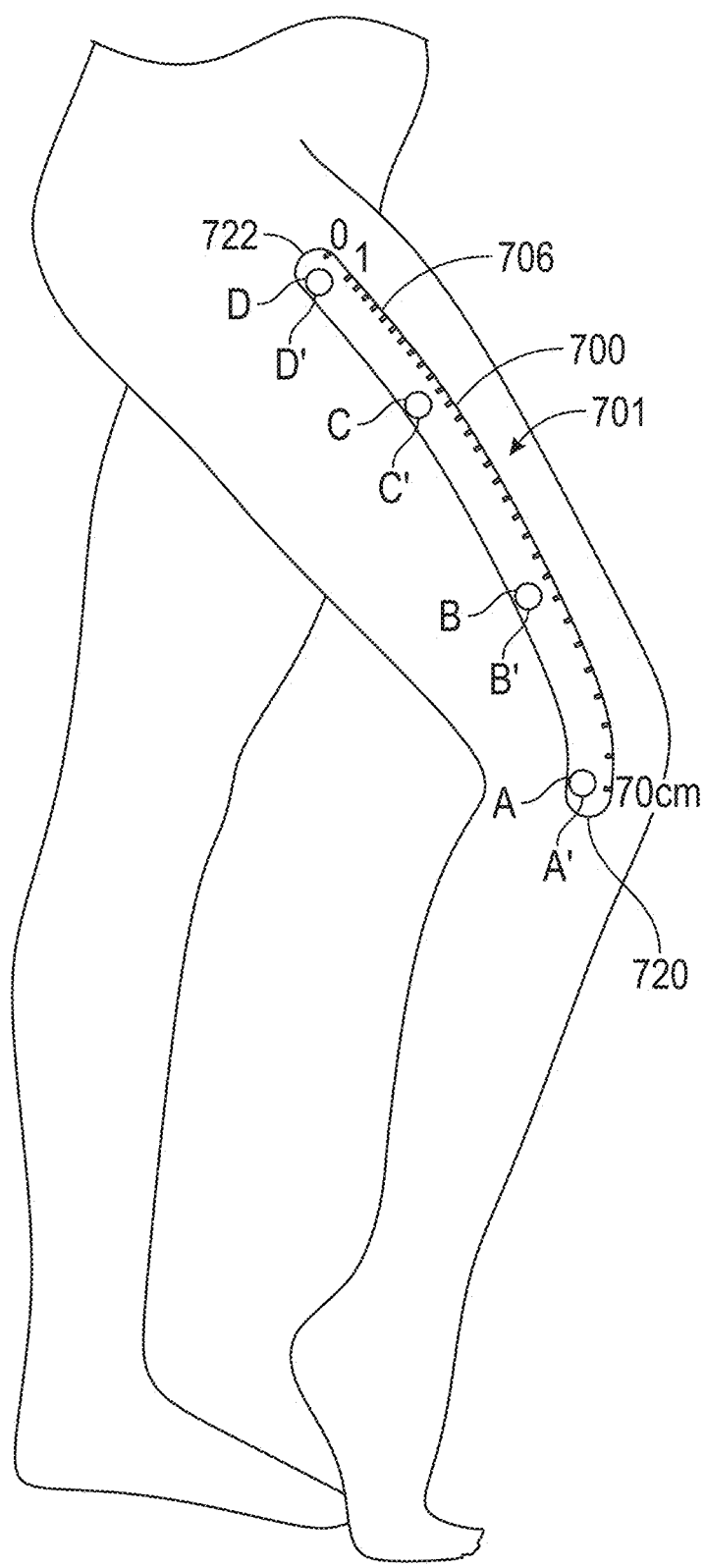
FIG. 7 is an illustration of a measuring device positioned along a thigh of a patient according to one embodiment of the invention.

FIG. 7 illustrates an embodiment of a measuring device 700 that comprises a single measuring tape 701 having a plurality of measurement marks 706 for measuring a distance and/or a length of, for example, a vessel. Each of the measurement marks 706 is positioned the same distance from an adjacent measurement mark 706. According to one embodiment, each of the measurement marks 706 is positioned 1 centimeter from an adjacent measurement mark 706. According to one embodiment, the single measuring tape 701 is 70 cm in length, with a first measurement mark 706 starting at 0 cm and a last measurement mark 706 ending at 70 cm, with a plurality of measurement marks 706 between the 0 cm mark and the 70 cm mark.

As further shown in FIG. 7, the single measuring tape 701 further includes a plurality of circular indicators (A/A', B/B', C/C', D/D') for measuring a diameter of, for example, a lumen of a vessel. As shown in the embodiment of FIG. 7, the plurality of circular indicators (A/A', B/B', C/C', D/D') are differing sizes from each other, with the circular indicators (A/A', B/B', C/C', D/D') increasing in size from a distal end 720 to a proximal end 722 of the device 700. According to an embodiment, the plurality of circular indicators (A/A', B/B', C/C', D/D') for measuring diameters and/or lumens comprise radiopaque markers and/or spheres. For example, according to one embodiment, the circular indicator A (or radiopaque sphere/marker) at the distal end 720 of the measuring tape 701 is 5 mm in diameter, with the circular indicators thereafter (i.e., B, C, D) increasing in size, e.g., (i) the circular indicator B (or radiopaque sphere/marker) is 6 mm in diameter, (ii) the circular indicator C (or radiopaque sphere/marker) is 7 mm in diameter, and (iii) the circular indicator D (or radiopaque sphere/marker), which is at the proximal end 722 of the measuring tape 710, is 8 mm in diameter. According to another embodiment, a circular indicator A' (or radiopaque sphere/marker) at the distal end 720 of the measuring tape 701 is 5 mm in diameter, with the circular indicators thereafter (i.e., B', C', D') increasing in size, e.g., (i) the circular indicator B' (or radiopaque sphere/marker) is 5.5 mm in diameter, (ii) the circular indicator C' (or radiopaque sphere/marker) is 6 mm in diameter, and (iii) the circular indicator D' (or radiopaque sphere/marker), which is at the proximal end 722 of the measuring tape 710, is 6.5 mm in diameter. As shown in the embodiment of FIG. 7, the measuring device 700 comprising the single measuring tape 701 can be positioned along a thigh of a patient in order to measure (i) a distance and/or a length of a vessel within the thigh of the patient using the plurality of measurement marks 706 and (ii) a diameter of a lumen of a vessel within the thigh of the patient using the plurality of circular indicators (A/A', B/B', C/C', D/D').

Figure 8:
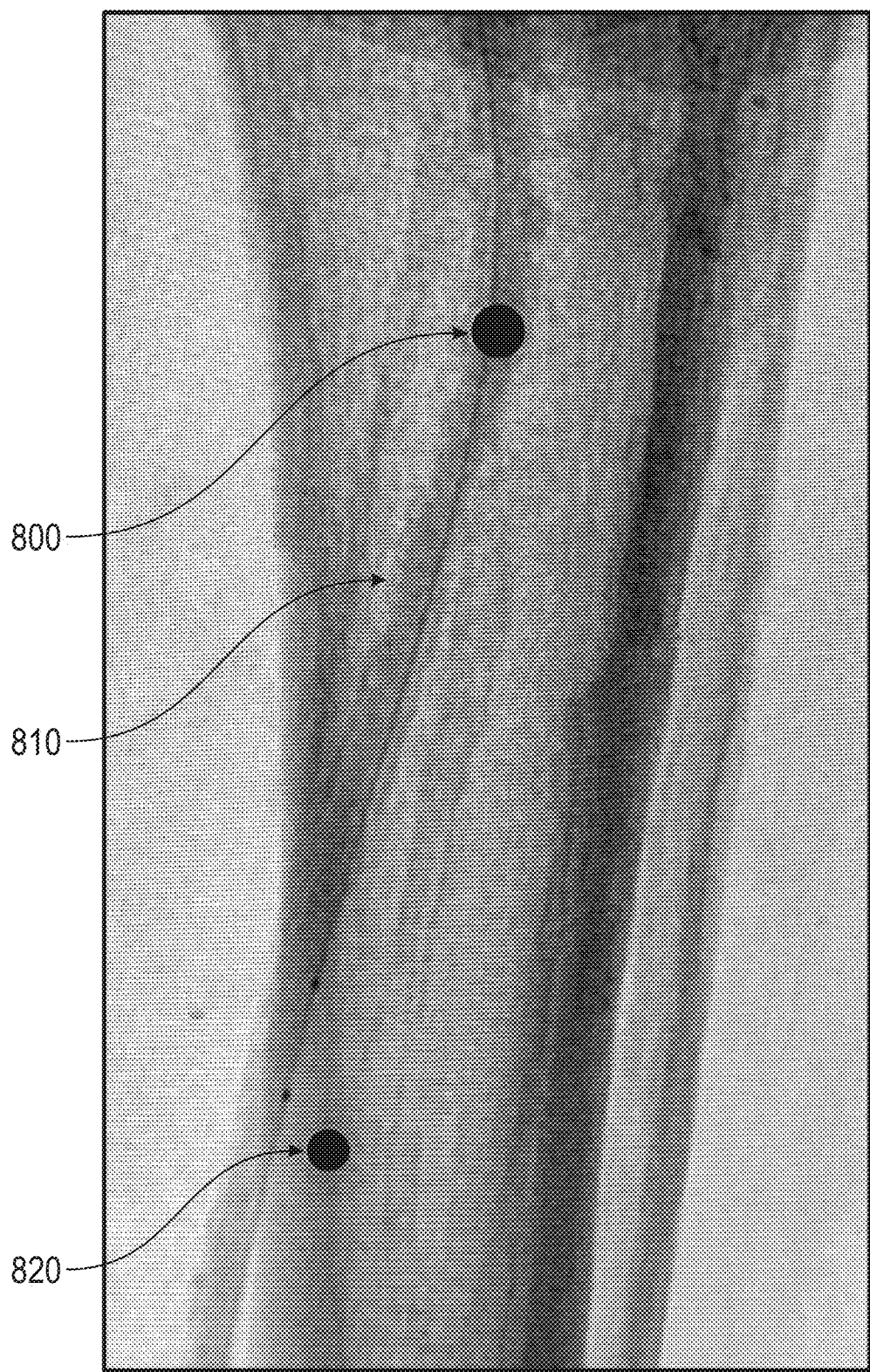
FIG. 8 is a photograph of an x-ray of a portion of a patient's leg having an inflatable balloon inserted into a vessel of the patient with two spheres of a measuring device superimposed on to the vessel of the patient's leg according to one embodiment of the invention.

FIG. 8 is a photograph of an x-ray of a portion of a patient's leg having a balloon inserted into a vessel of the patient with two spheres of a measuring device superimposed on to the vessel of the patient's leg according to one embodiment of the invention. According to this embodiment, a balloon has been inserted into a vessel of the patient in order to inflate or expand the balloon for treating the vessel (e.g., for a balloon angioplasty of a certain vessel). In the image of the embodiment of FIG. 8, a cylindrical balloon 810, which is inserted into a vessel of the patient's leg, has been inflated to a diameter of four millimeters (mm). As also shown in the embodiment of FIG. 8, a four millimeter (mm) sphere 800 (i.e., a sphere having a circumference of 4 mm) of a measuring device is superimposed along an upper portion of the vessel and the inserted and inflated balloon 810, while a 3.5 millimeter (mm) sphere 820 (i.e., a sphere having a circumference of 3.5 mm) of a measuring device is superimposed along a lower portion of the vessel and the inserted and inflated balloon 810. The four millimeter (mm) balloon 800 and/or the 3.5 millimeter (mm) sphere 820 are being used to measure the diameter of the inserted balloon 810 in a two-dimensional (2D) view. These superimposed spheres (800, 820) and any other spheres can assist in measuring cylindrical and/or circumferential diameters of an inserted and/or inflated balloon, a lumen or vessel, and/or a mass using, e.g., x-ray directed to the two targets to be measured from any angle. As shown in the image of FIG. 8, the four millimeter (mm) sphere 800 lays directly over the inserted and inflated balloon 810. Thus, the four millimeter (mm) sphere 800, which is superimposed onto the inserted and inflated balloon 810, is an exact approximation of the balloon 810, which has been inflated to four millimeters (mm) in diameter. The four millimeter (mm) sphere 800 thereby confirms the inflated diameter of the balloon 810, as it would confirm the diameter of the lumen of the vessel or the diameter of any mass or lumen. By contrast, the 3.5 millimeter (mm) sphere 820, which has also been superimposed onto the inserted and inflated balloon 810, is clearly smaller than the balloon 810, which has been inflated to four millimeters (mm). In particular, the 3.5 millimeter (mm) sphere 820 is located to the side of the inserted and inflated balloon 810, which has been inflated to four millimeters (mm) in diameter. Since this sphere 820 is only 3.5 millimeters (mm) in diameter, when visually compared to the inserted and inflated balloon 810, which has been inflated to four millimeters (mm) in diameter, the size deferential between the two is very evident. Thus, according to embodiments of the measuring device discussed herein, the idea of having different sizes of circular indicators (or spheres) located at different intervals along a measuring device assist an operator in deciphering the difference in size between an inserted and inflated, cylindrical shaped balloon (or a vessel lumen) in comparison to the respective circular indicator (or sphere). According to the embodiment of FIG. 8, the proposed measuring device and associated circular indicators (or spheres) assists an operator in making decisive measurement decisions that could lead an operator to increase and/or decrease the size of a device or a tool (e.g., an inflatable balloon) quickly. Moreover, according to embodiments of the invention, the circular indicator (or sphere) could provide an accurate measurement a majority of the time regardless of the angles used to visualize the circular indicator (or sphere), under, e.g., x-ray or other visualization techniques.

Figure 9:
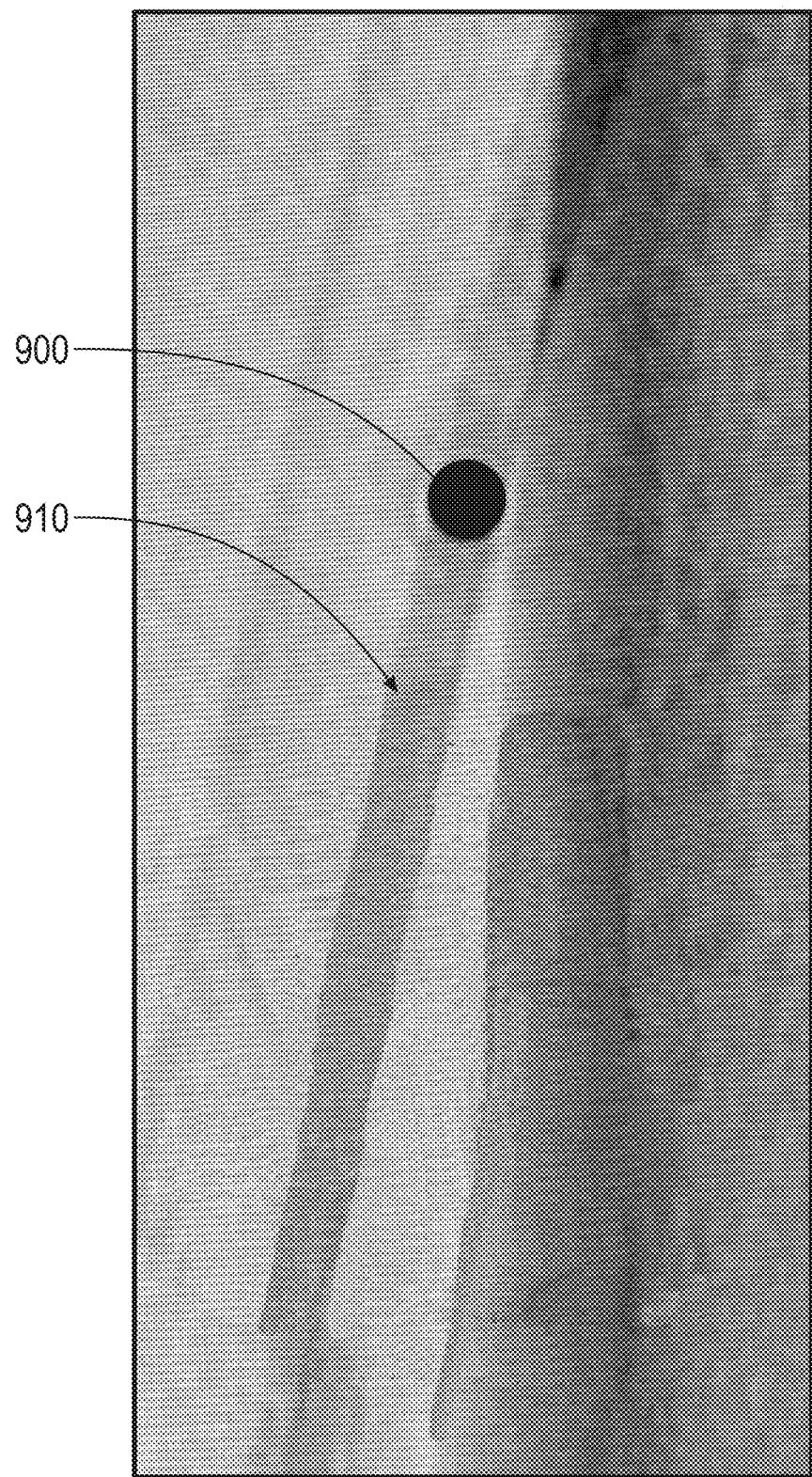
FIG. 9 is a photograph of an x-ray of a portion of a patient's leg having an inflatable balloon inserted into a vessel of the patient with a single sphere of a measuring device superimposed on to the vessel of the patient's leg according to one embodiment of the invention.

FIG. 9 is a photograph of an x-ray of a portion of a patient's leg having a balloon inserted into a vessel of the patient with a single sphere of a measuring device superimposed on to the vessel of the patient's leg according to one embodiment of the invention. According to this embodiment, a balloon has been inserted into a vessel of the patient in order to inflate or expand the balloon for treating the vessel (e.g., for a balloon angioplasty of a certain vessel). In the image of the embodiment of FIG. 9, a cylindrical balloon 910, which has been inflated to three millimeters (mm) in diameter, is inserted into a vessel of the patient's leg. As also shown in the embodiment of FIG. 9, a three millimeter (mm) sphere 900 of a measuring device is superimposed along a portion of the vessel and the inserted and inflated balloon 910. As shown in the image of FIG. 9, the three millimeter (mm) sphere 900 superimposed onto the inserted and inflated balloon 910 is an exact approximation of the balloon 910, which has been inflated to three millimeters (mm) in diameter. According to this embodiment, the spheres of the measuring device of the invention provide both simplicity and effectiveness that make the measuring method and measuring device of the invention an easier way to get answers and measurements quickly and accurately. For example, as shown in the image of FIG. 9, the three millimeter (mm) sphere 900 superimposed onto the inserted and inflated balloon 910 provides a simple and effective method to quickly and accurately determine whether the inserted and inflated balloon 910 has been inflated to the desired amount, e.g., three millimeters (mm).

Figure 10:
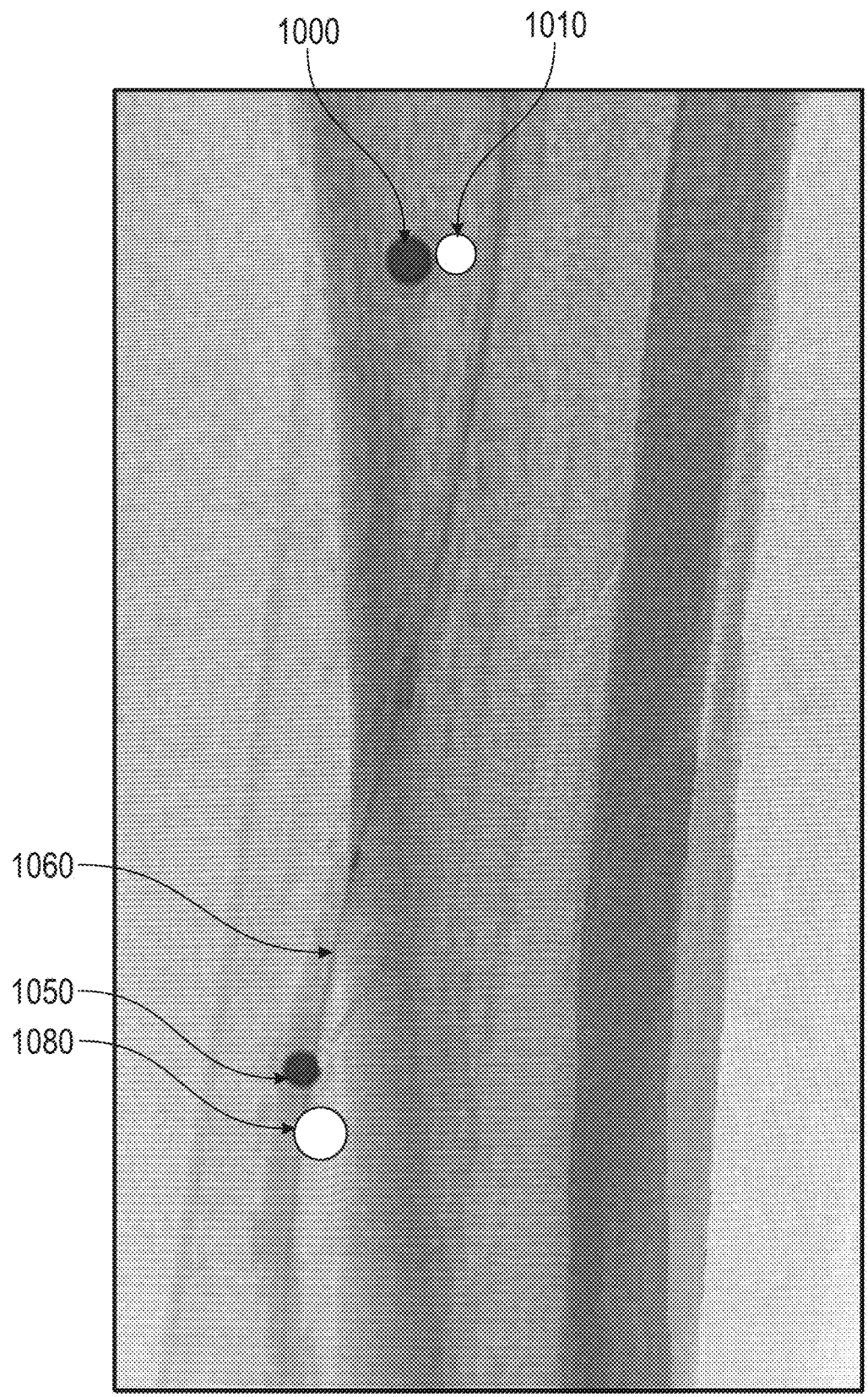
FIG. 10 is a photograph of an x-ray of a portion of a patient's leg having an inflatable balloon inserted into a vessel of the patient with a plurality of spheres of a measuring device superimposed on to the vessel of the patient's leg according to one embodiment of the invention.

FIG. 10 is a photograph of an x-ray of a portion of a patient's leg having a balloon inserted into a vessel of the patient with a plurality of spheres of a measuring device superimposed on to the vessel of the patient's leg according to one embodiment of the invention. According to this embodiment, a balloon has been inserted into a vessel of the patient in order to inflate or expand the balloon for treating the vessel (e.g., for a balloon angioplasty of a certain vessel). In the image of the embodiment of FIG. 10, a cylindrical balloon 1060, which has been inflated to 3.5 millimeters (mm) in diameter, is inserted into a vessel of the patient's leg. As shown in the embodiment of FIG. 10, a four millimeter (mm) sphere 1000 of a measuring device is superimposed along an upper portion of the vessel and the inserted and inflated balloon 1060, while a 3.5 millimeter (mm) sphere 1010 of a measuring device is superimposed alongside of the superimposed four millimeter (mm) sphere 1000. As also shown in the embodiment of FIG. 10, a 3.5 millimeter (mm) sphere 1050 of a measuring device is superimposed along a lower portion of the vessel and the inserted and inflated balloon 1060, while a four millimeter (mm) sphere 1080 of a measuring device is superimposed adjacent to the superimposed 3.5 millimeter (mm) sphere 1050. As shown in the image of FIG. 10, the 3.5 millimeter (mm) sphere 1010 superimposed alongside of the four millimeter (mm) sphere 1000, which is superimposed along an upper portion of the vessel and the inserted and inflated balloon 1060, clearly illustrates the differences in the circumferences of the two spheres (i.e., the 3.5 millimeter (mm) sphere 1010 versus the four millimeter (mm) sphere 1000). The differences in the circumferences of the two spheres (i.e., the 3.5 millimeter (mm) sphere 1010 versus the four millimeter (mm) sphere 1000) is very clear, which is one of the many benefits of the unique measuring device of the instant application. As also shown in the image of FIG. 10, the 3.5 millimeter (mm) sphere 1050, which is superimposed along a lower portion of the vessel and the inserted and inflated balloon 1060, is an exact approximation of the balloon 1060, which has been inflated to 3.5 millimeters (mm) in diameter. This comparison of the superimposed 3.5 millimeter (mm) sphere 1050 to the inserted and inflated balloon 1060 confirms the equality (i.e., the equality in the diameter or circumference of these elements), which is critical in any medical procedure. By contrast, the four millimeter (mm) sphere 1080, which has been superimposed adjacent to the superimposed 3.5 millimeter (mm) sphere 1050, is clearly larger than the balloon 1060, which has been inflated to 3.5 millimeters (mm) in diameter. This comparison of the superimposed four millimeter (mm) sphere 1080 (as well as the superimposed 3.5 millimeter (mm) sphere 1050) to the inserted and inflated balloon 1060, allows for a quick and efficient method to quickly and accurately determine whether the inserted and inflated balloon 1060 has been inflated to the desired amount, e.g., 3.5 millimeters (mm).

Figure 11A:
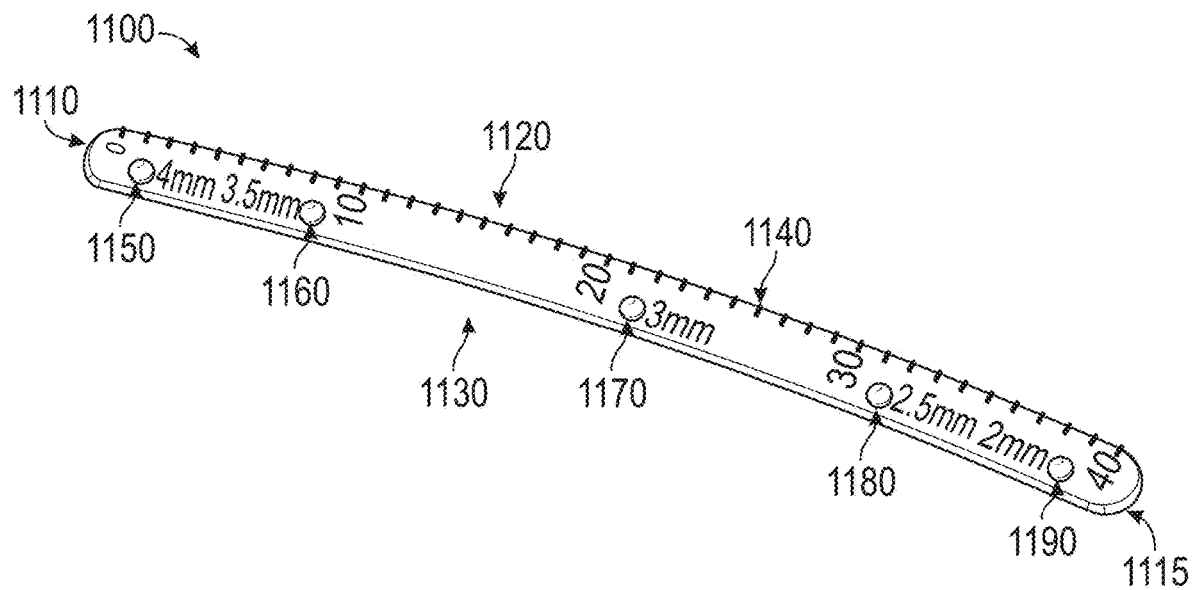
FIG. 11A is an illustration of a measuring device according to one embodiment of the invention.

FIG. 11A illustrates an embodiment of a measuring device 1100 that comprises a single measuring tape having (i) a plurality of measurement marks 1140, along a first side 1120 of the measuring device 1100, for measuring a distance and/or a length of, for example, a vessel, and (ii) a plurality of circular indicators (or spheres) (1150, 1160, 1170, 1180, 1190), along a second side 1130 of the measuring device 1100, for measuring a diameter of, for example, a lumen of a vessel. Each of the measurement marks 1140 is positioned the same distance from an adjacent measurement mark 1140. According to one embodiment, each of the measurement marks 1140 is positioned 1 centimeter from an adjacent measurement mark 1140. According to an embodiment, one or more of the measurement marks 1140 of the plurality of measurement marks 1140 comprises a number (see, e.g., numbers "0," "10," "20," "30," and "40"). In the embodiment of FIG. 11A, the measuring device 1100 is shown with a curved edge(s) (see, e.g., first and second sides 1120 and 1130). This curve of the measuring device 1100 allows for the measuring device 1100 to accommodate the anatomy of, e.g., a vessel and/or various body parts, including, e.g., the leg below the knee, which has a variation of curvatures. For example, the curve of the measuring device 1100 is equal to the anatomical curve of a vessel and/or a certain body part(s).

As also shown in the embodiment of FIG. 11A, the measuring device 1100 includes the plurality of circular indicators (or spheres) (1150, 1160, 1170, 1180, 1190), which are differing sizes from each other, with the circular indicators (1150, 1160, 1170, 1180, 1190) decreasing in size from a left side to a right side of the device 1100. For example, as shown in the embodiment of FIG. 11A, the first circular indicator 1150 positioned at a distal end 1110 (i.e., left side) of the measuring device 1100 is 4 mm in diameter, the second circular indicator 1160 is 3.5 mm in diameter, the third circular indicator 1170 near the mid-point of the measuring device 1100 is 3 mm in diameter, the fourth circular indicator 1180 is 2.5 mm in diameter, and the fifth circular indicator 1190 positioned at a proximal end 1115 (i.e., right side) of the measuring device 1100 is 2 mm in diameter. According to an embodiment, the plurality of circular indicators (1150, 1160, 1170, 1180, 1190) for measuring diameters and/or lumens comprise radiopaque markers.

Figure 11B:
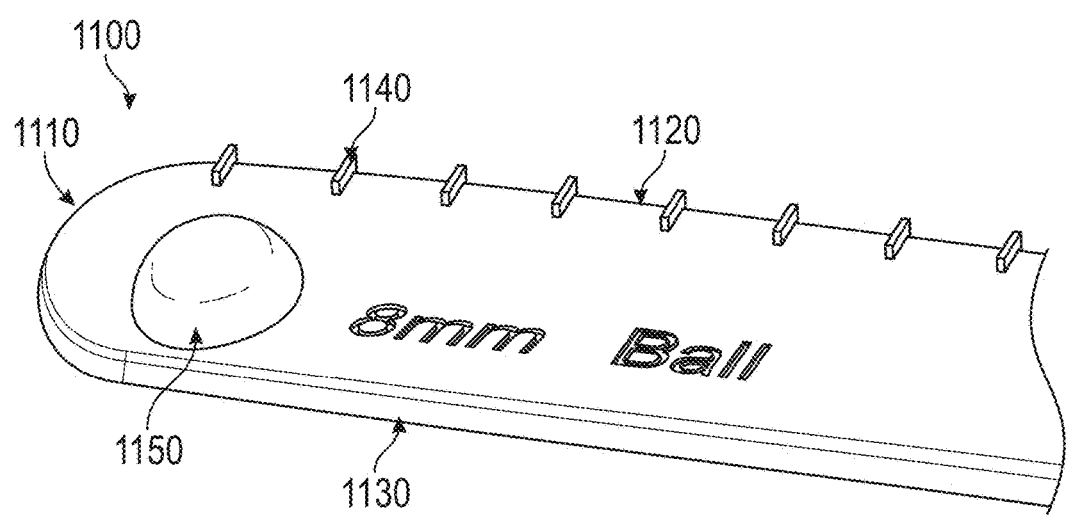
FIG. 11B is an illustration of an exploded, partial view of a portion of the measuring device of FIG. 11A according to an embodiment of the invention.

FIG. 11B illustrates an exploded, partial view of the first circular indicator (or sphere) 1150, which is positioned at the distal end 1110 (i.e., left side) of the measuring device 1100 of FIG. 11A. According to this embodiment, this first circular indicator (or sphere) 1150 is 8 mm in diameter (as opposed to the 4 mm circular indicator (or sphere) discussed above). Also shown in the exploded, partial view of FIG. 11B are a portion of the plurality of measurement marks 1140 that are positioned along the first side 1120 of the measuring device 1100.

Figure 12A:
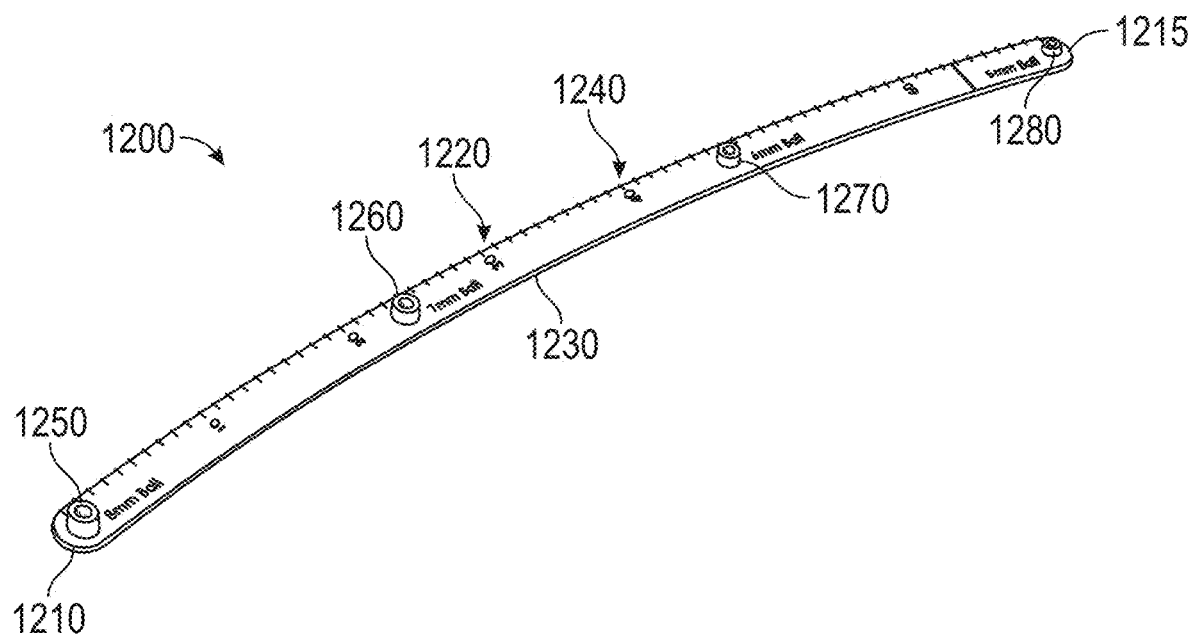
FIG. 12A is an illustration of a measuring device according to one embodiment of the invention.

FIG. 12A illustrates an embodiment of a measuring device 1200 that comprises a single measuring tape having (i) a plurality of measurement marks 1240, along a first side 1220 of the measuring device 1200, for measuring a distance and/or a length of, for example, a vessel, and (ii) a plurality of cylindrical elements or tubes (1250, 1260, 1270, 1280), along a second side 1230 of the measuring device 1200, for measuring a diameter of, for example, a lumen of a vessel. Each of the measurement marks 1240 is positioned the same distance from an adjacent measurement mark 1240. According to one embodiment, each of the measurement marks 1240 is positioned 1 centimeter from an adjacent measurement mark 1240. According to an embodiment, one or more of the measurement marks 1240 of the plurality of measurement marks 1240 comprises a number (see, e.g., numbers "10," "20," "30," and "40"). According to one embodiment, the measuring device 1200 of FIG. 12A can be used for measuring vessels and/or lumens in an area of the leg above the knee. Thus, according to an embodiment, the measuring device 1200 of FIG. 12A is longer than, for example, the measuring device 1100 of FIG. 11. Moreover, in the embodiment of FIG. 12A, the measuring device 1200 is shown with a curved edge(s) (see, e.g., first and second sides 1220 and 1230). This curve of the measuring device 1200 allows for the measuring device 1200 to accommodate the anatomy of, e.g., a vessel and/or various body parts, including, e.g., vessels of the leg above the knee, which has a different variation of curvatures than those of the area below the knee. For example, the curve of the measuring device 1200 is equal to the anatomical curve of a vessel and/or a certain body part(s).

As also shown in the embodiment of FIG. 12A, measuring device 1200 includes the plurality of cylindrical elements or tubes (1250, 1260, 1270, 1280), which are each configured to house a certain size measuring sphere (or ball) for measuring a diameter of, for example, a lumen of a vessel. According to this embodiment, the measuring spheres (or balls) are housed in a unique housing by trapping or embedding the sphere within a short cylindrical element or tube (1250, 1260, 1270, 1280), which has a designed cover or filling on top of the sphere, filling all empty spaces surrounding the sphere which causes the sphere to be stationary and not move within the housing or cylindrical element or tube (1250, 1260, 1270, 1280). Thus, by using the cylindrical elements or tubes (1250, 1260, 1270, 1280) to house the measuring sphere (or ball), it is dependable that the measuring sphere (or ball) will be in the same location at all times. This unique filling material allows for easily housing and embedding the measuring sphere (or ball) within the spaces provided within the short cylindrical elements or tubes (1250, 1260, 1270, 1280). According to one embodiment, the filling material comprises a non-fluoroscopic (or non-radiopaque) material, such as, e.g., a plastic material (including, e.g., polyethylene), that allows for the measuring sphere (or ball) to be stabilized within the respective cylindrical element or tube, such that the measuring sphere (or ball) is unable to move, and such that the filling material does not interfere with the visualizing of the sphere under, e.g., x-ray.

As shown in the embodiment of FIG. 12A, the measuring device 1200 includes the plurality of cylindrical elements or tubes (1250, 1260, 1270, 1280) to house variable spheres that differ in sizes from each other, with the spheres of the cylindrical elements or tubes (1250, 1260, 1270, 1280) decreasing in size from a left side to a right side of the device 1200. For example, as shown in the embodiment of FIG. 12A, the first cylindrical element or tube 1250, which is positioned at a distal end 1210 (i.e., left side) of the measuring device 1200, houses an embedded sphere (or ball) that is 8 mm in diameter, the second cylindrical element or tube 1260 houses an embedded sphere (or ball) that is 7 mm in diameter, the third cylindrical element or tube 1270 houses an embedded sphere (or ball) that is 6 mm in diameter, and the fourth cylindrical element or tube 1280, which is positioned at a proximal end 1215 (i.e., right side) of the measuring device 1200, houses an embedded sphere (or ball) that is 5 mm in diameter. According to an embodiment, the spheres (or balls) that are housed within the plurality of cylindrical elements or tubes (1250, 1260, 1270, 1280), respectively, for measuring diameters and/or lumens comprise radiopaque markers.

Figure 12B:
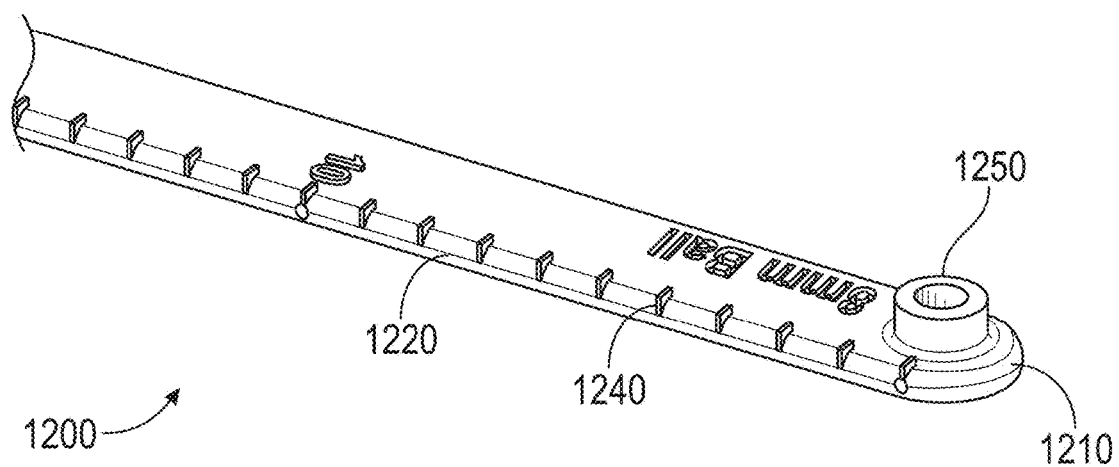
FIG. 12B is an illustration of an exploded, partial view of a portion of the measuring device of FIG. 12A according to an embodiment of the invention.

FIG. 12B illustrates an exploded, partial view of the first cylindrical element or tube 1250, which is positioned at the distal end 1210 (i.e., left side) of the measuring device 1200 of FIG. 12A. As discussed above, this first cylindrical element or tube 1250 houses a sphere (or ball) that is 8 mm in diameter. Also shown in the exploded, partial view of FIG. 12B are a portion of the plurality of measurement marks 1240 that are positioned along the first side 1220 of the measuring device 1200.

As discussed above, the measuring device 1100 of FIGS. 11A and 11B as compared to the measuring device 1200 of FIGS. 12A and 12B provide two different methods to secure the measuring sphere (or ball) within the measuring device (or tape) 1100 or 1200. According to the embodiment of the measuring device 1100 of FIGS. 11A and 11B, which is one method of securing a measuring sphere (or ball) within the measuring device (or tape) 1100, a sphere (or ball) is placed within a short cylindrical tube, which is then filled with a non-radiopaque material to keep the sphere stationary in all positions. Thereafter, a dome is added to make the short cylindrical tube, which includes the sphere (or ball) and the filled material, smooth and to enclose the sphere (or ball) (see, e.g., dome of circular indicator 1150 of FIG. 11B). By contrast, according to the embodiment of the measuring device 1200 of FIGS. 12A and 12B, which is a second method of securing a measuring sphere (or ball) within the measuring device (or tape) 1200, in this method or concept, a sphere (or ball) is dropped into a short cylindrical tube and thereafter, non-radiopaque material is added to enclose (or embed) the sphere (or ball) in position always. According to this embodiment of the measuring device 1200 of FIGS. 12A and 12B, no additional dome is added to the short cylindrical tube (see, e.g., cylindrical element or tube 1250 of FIG. 12B).

Figure 13:
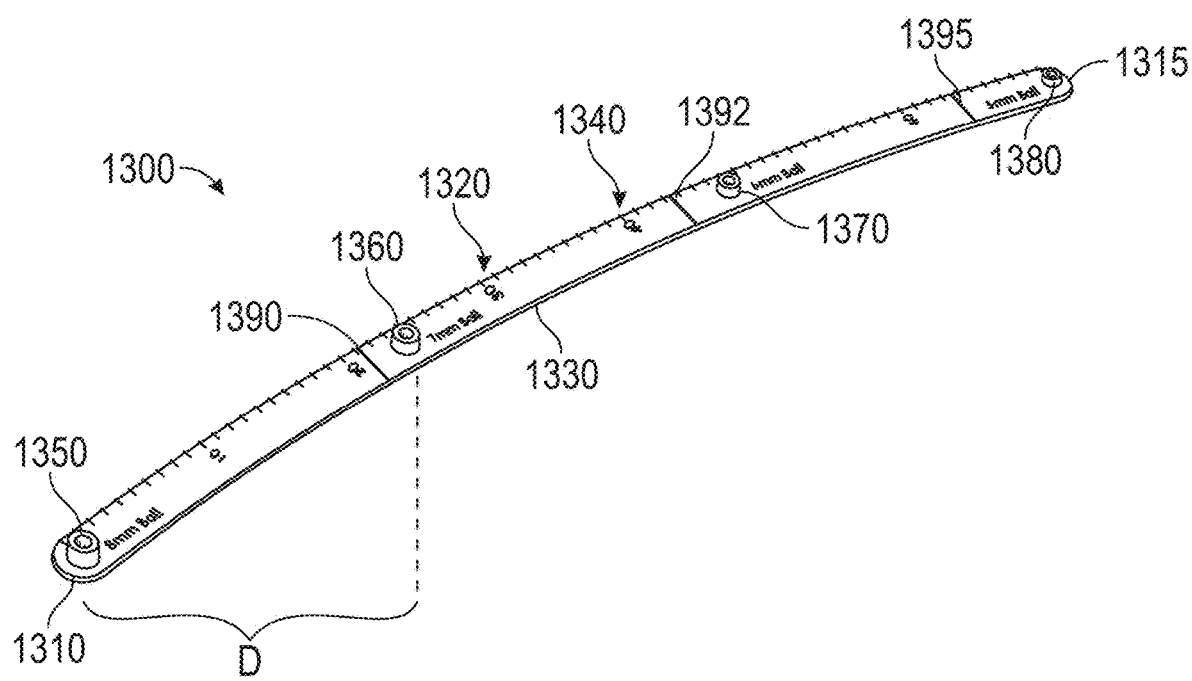
FIG. 13 is an illustration of a measuring device according to one embodiment of the invention.

FIG. 13 illustrates an embodiment of a measuring device 1300 that comprises a single measuring tape having (i) a plurality of measurement marks 1340, along a first side 1320 of the measuring device 1300, for measuring a distance and/or a length of, for example, a vessel, and (ii) a plurality of cylindrical elements or tubes (1350, 1360, 1370, 1380), along a second side 1330 of the measuring device 1300, for measuring a diameter of, for example, a lumen of a vessel. Each of the measurement marks 1340 is positioned the same distance from an adjacent measurement mark 1340. According to one embodiment, each of the measurement marks 1340 is positioned 1 centimeter from an adjacent measurement mark 1340. According to an embodiment, one or more of the measurement marks 1340 of the plurality of measurement marks 1340 comprises a number (see, e.g., numbers "10," "20," "30," and "40").

As also shown in the embodiment of FIG. 13, the measuring device 1300 includes the plurality of cylindrical elements or tubes (1350, 1360, 1370, 1380), which are each configured to house a certain size measuring sphere (or ball) for measuring a diameter of, for example, a lumen of a vessel. According to this embodiment, the measuring spheres (or balls) are housed in a unique housing by trapping or embedding the sphere within a short cylindrical element or tube (1350, 1360, 1370, 1380), which has a designed cover on top of the sphere filling all empty spaces surrounding the sphere which causes the sphere to be stationary and not move within the housing or cylindrical element or tube (1350, 1360, 1370, 1380). Thus, by using the cylindrical elements or tubes (1350, 1360, 1370, 1380) to house the measuring sphere (or ball), it is dependable that the measuring sphere (or ball) will be in the same location at all times. This unique filling allows for easily housing and embedding the measuring sphere (or ball) within the spaces provided within the short cylindrical elements or tubes (1350, 1360, 1370, 1380).

According to the embodiment of FIG. 13, the plurality of cylindrical elements or tubes (1350, 1360, 1370, 1380) house spheres that differ in sizes from each other, with the spheres of the cylindrical elements or tubes (1350, 1360, 1370, 1380) decreasing in size from a left side to a right side of the device 1300. For example, as shown in the embodiment of FIG. 13, the first cylindrical element or tube 1350, which is positioned at a distal end 1310 (i.e., left side) of the measuring device 1300, houses an embedded sphere (or ball) that is 8 mm in diameter, the second cylindrical element or tube 1360 houses an embedded sphere (or ball) that is 7 mm in diameter, the third cylindrical element or tube 1370 houses an embedded sphere (or ball) that is 6 mm in diameter, and the fourth cylindrical element or tube 1380, which is positioned at a proximal end 1315 (i.e., right side) of the measuring device 1300, houses an embedded sphere (or ball) that is 5 mm in diameter. According to an embodiment, the spheres (or balls) that are housed within the plurality of cylindrical elements or tubes (1350, 1360, 1370, 1380), respectively, for measuring diameters and/or lumens comprise radiopaque markers.

In the measuring device 1300 of the embodiment of FIG. 13, each of the plurality of cylindrical elements or tubes (1350, 1360, 1370, 1380), which house the respective embedded spheres (or balls), are positioned a certain distance or interval (D) from each other. For example, according to one embodiment, the distance or interval (D) is in a range of 50 mm to 100 mm, which allows for adjustment of the distance or interval (D) between the respective cylindrical elements or tubes (1350, 1360, 1370, 1380) housing the respective spheres to correspond to, for example, the area of a patient's leg above the knee where intervals between the cylindrical elements or tubes (1350, 1360, 1370, 1380) housing the respective spheres is reasonable to be at around 100 mm. According to another embodiment, the intervals between the cylindrical elements or tubes (1350, 1360, 1370, 1380) housing the respective spheres when the measuring device 1300 is being used below the knee is more suitable to be at least within a range between 50 mm to 75 mm to accommodate the faster tapering in the tibial and pedal arteries.

As also shown in the embodiment of FIG. 13, the measuring device 1300 includes a plurality of indentations or grooves (1390, 1392, 1395). These indentations or grooves (1390, 1392, 1395) are provided to make it possible to fold the measuring device 1300 (either long or short versions of the measuring device 1300 (i.e., the measuring device 1200 or 1300 of FIGS. 12A and 13 versus the shorter measuring device 1100 of FIG. 11)) onto itself during packaging, which reduces the space needed for longer storage and/or transportation. In addition to the packaging benefits, these indentations or grooves (1390, 1392, 1395) play a critical role in accommodating the variable angles, curves, and/or tortuosity(ies) of the body, while still providing an accurate measurement (e.g., length and/or distance) of the specific body part. For example, the 90-degree angle at the ankle joint is an example of the variable angles, curves, and/or tortuosity of the body that can be accommodated by the indentations or grooves (1390, 1392, 1395) of the measuring device 1300, along with the variations of multiple smaller angles along the surface areas of the body at which the measuring device 1300 may be placed and used.

Figure 14A:
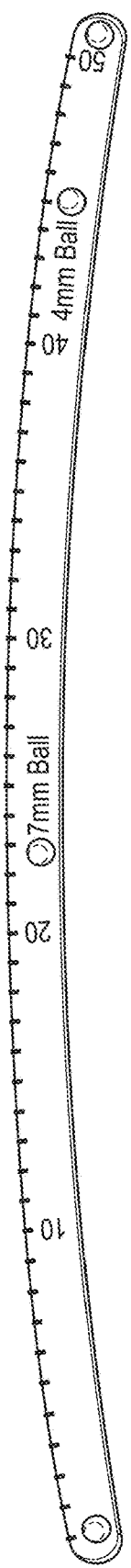
FIG. 14A is an illustration of a measuring device according to one embodiment of the invention.
Figure 14B:
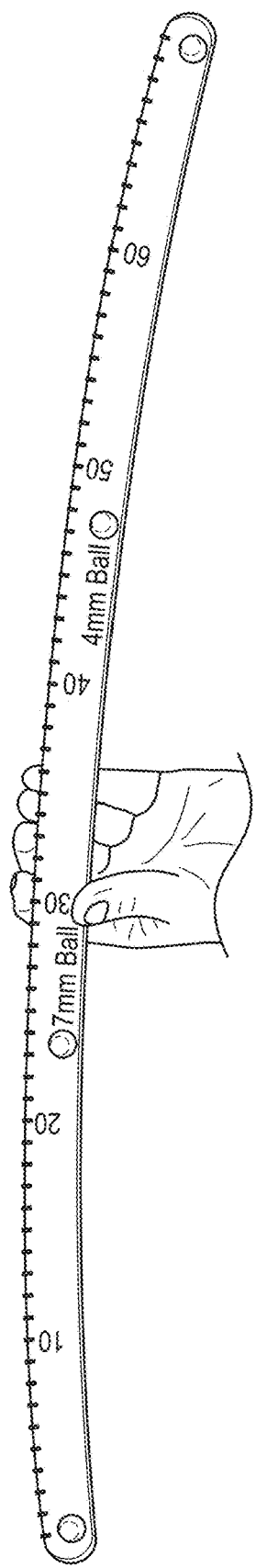
FIG. 14B is an illustration of a measuring device according to one embodiment of the invention.

FIGS. 14A and 14B illustrate two embodiments of a measuring device. In the embodiment of FIG. 14A, a measuring device 1400A is provided that can be used for a below the knee measurement tape with included circular indicators (or spheres). According to the embodiment of FIG. 14A, the measuring device 1400A has a length of 30 cm to 50 cm. A 30 cm length measuring device or tape 1400A allows for measuring from below the knee to the ankle, while a 50 cm length measuring device or tape 1400A allows for measuring to a level below the ankle.

In the embodiment of FIG. 14B, a measuring device 1400B is provided that can be used for an above the knee measurement tape with included circular indicators (or spheres). According to the embodiment of FIG. 14B, the measuring device 1400B has a length of 50 cm to 70 cm. A 50 cm length measuring device or tape 1400B allows for measuring to a level of the knee joint, while a 70 cm length measuring device or tape 1400B allows for measuring to a level below the knee, which includes the proximal tibial arteries and can include the below the knee popliteal artery as well.

Figure 15:
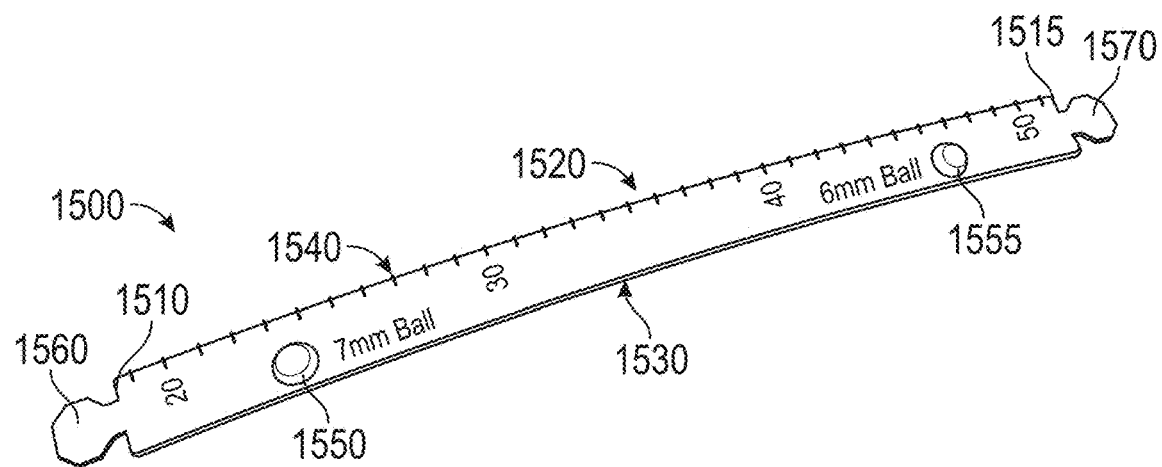
FIG. 15 is an illustration of a measuring device according to one embodiment of the invention.

FIG. 15 illustrates an embodiment of a measuring device 1500 that comprises a single measuring tape having (i) a plurality of measurement marks 1540, along a first side 1520 of the measuring device 1500, for measuring a distance and/or a length of, for example, a vessel, and (ii) a pair of circular indicators (1550, 1555) along a second side 1530 of the measuring device 1500, for measuring a diameter of, for example, a lumen of a vessel. According to this embodiment, the measuring device 1500 further includes (i) a first hinge connection member 1560 at a distal end 1510 (or left side) of the measuring device 1500, and (ii) a second hinge connection member 1570 at a proximal end 1515 (or right side) of the measuring device 1500. The first and second connection members (1560, 1570), which can also be in the form of hinge members, allow for the measuring device or tape 1500 to be folded during shipping and/or storage. The first and second connection members (1560, 1570) further allow for the measuring device or tape 1500 to accommodate 90 degree angles during measuring of various body vessels and/or lumens.

Figure 16A:
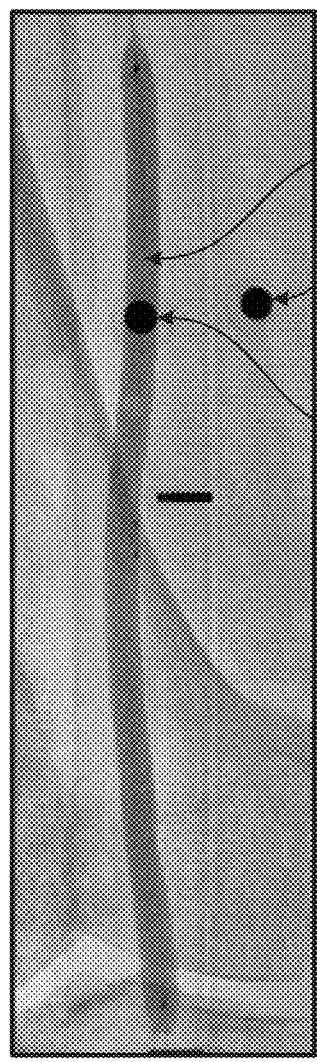
FIGS. 16A and 16B are photographs of an x-ray of a portion of a patient's leg having an inflatable balloon inserted into a vessel of the patient with two spheres of two different measuring devices superimposed on to the vessel of the patient's leg according to an embodiment of the invention.
Figure 16B:
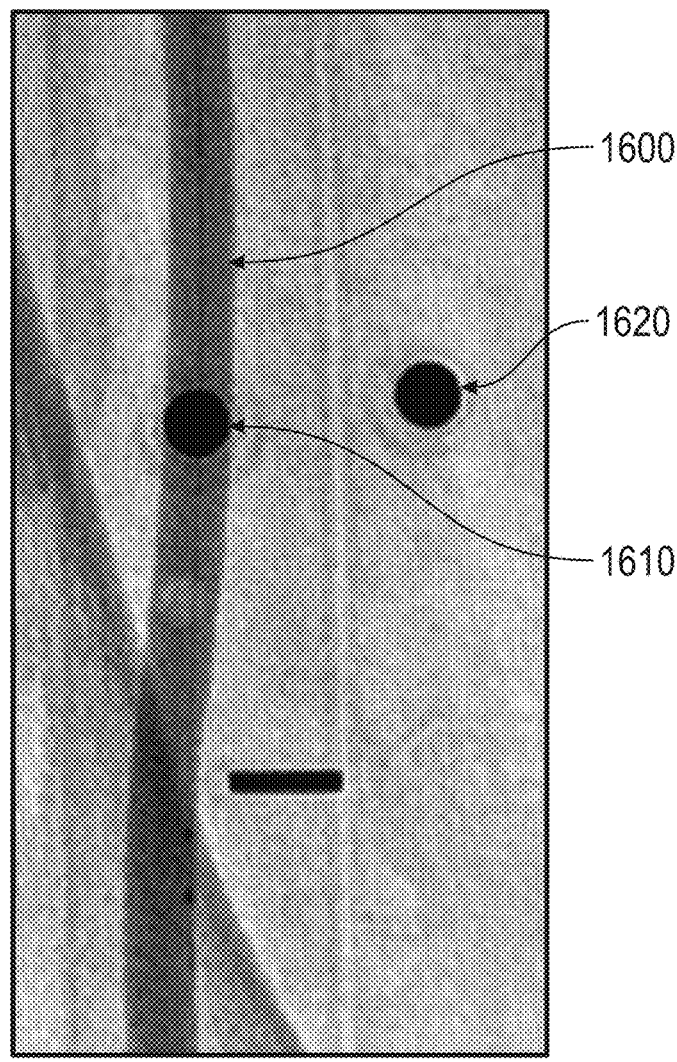

FIGS. 16A and 16B are photographs of an x-ray of a portion of a patient's leg having an inflatable balloon inserted into a vessel of the patient with two spheres of two different measuring devices superimposed on to the vessel of the patient's leg according to an embodiment of the invention. As shown in FIG. 16A, which is a non-magnified image of the portion of the patient's leg, a six millimeter (mm) sphere 1610 of a first measuring device, which is superimposed onto an inflated balloon 1600, is positioned next to a six millimeter (mm) sphere 1620 of a second measuring device. As shown in the image of FIG. 16A, each of the six millimeter (mm) spheres (1610, 1620) are precise in size, despite any angle of the x-ray, their image is achieved.

As shown in FIG. 16B, which is an x-ray image having both magnifications and angulations by the x-ray machine, there is no impact (zero impact) on the actual size of the six millimeter (mm) spheres (1610, 1620), as compared to the subject being measured by the spheres (1610, 1620) (e.g., the inflated balloon 1600). Thus, as long as both objects (e.g., the spheres (1610, 1620) and/or the inflated balloon 1600) are in the same x-ray field and the same angulation field while obtaining images, there is no impact (zero impact) on the actual size of the six millimeter (mm) spheres (1610, 1620).

Figure 17:
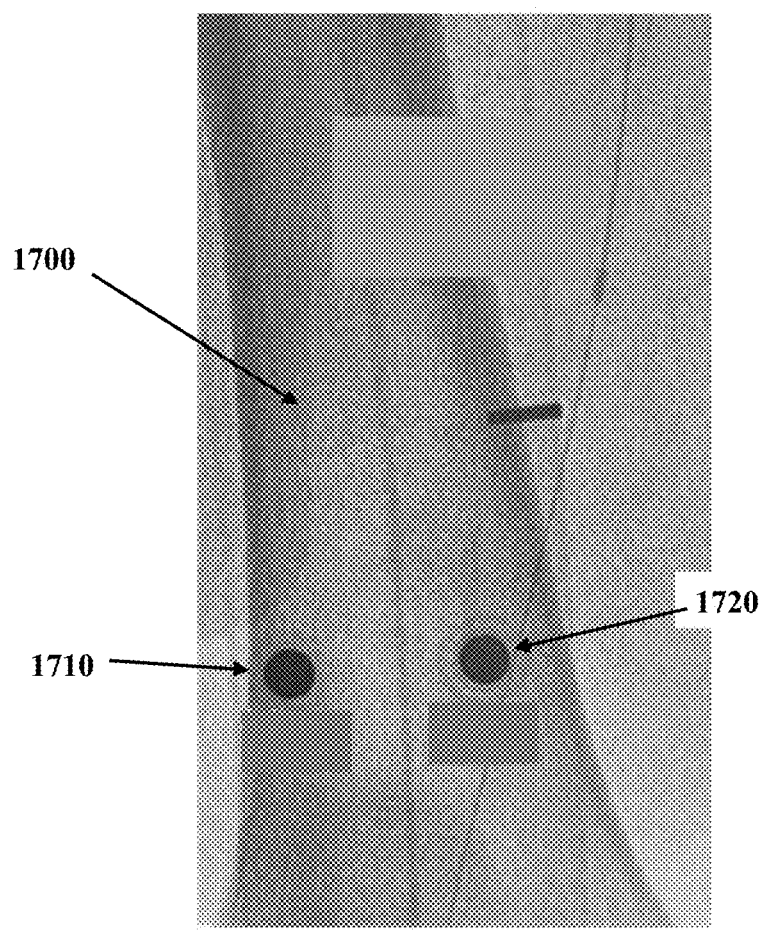
FIG. 17 is a photograph of an x-ray of a portion of a patient's leg having two spheres of a pair of measuring devices superimposed on to a vessel of the patient's leg according to one embodiment of the invention.

FIG. 17 is a photograph of an x-ray of a portion of a patient's leg having two spheres of a pair of measuring devices superimposed on to a vessel of the patient's leg according to one embodiment of the invention. As shown in FIG. 17, a subject 1700 (e.g., a patient's leg) is provided, along with a first measuring sphere 1710 and a second measuring sphere 1720. The first measuring sphere 1710, which is a six millimeter (mm) sphere disposed on a first measuring device (or tape or ruler), is positioned near, but separated from the second measuring sphere 1720, which is also a six millimeter (mm) sphere disposed on a second measuring device (or tape or ruler). Thus, the first measuring sphere 1710 of a first measuring device (or tape) and the second measuring sphere 1720 of a second measuring device (or tape) have the same sphere size. The first measuring sphere 1710 and the second measuring sphere 1720 are placed side-by-side for comparison, prior to introducing the study subject (such as, e.g., an inflated balloon). Since the first measuring sphere 1710 is equal in size to the second measuring sphere 1720, both the first measuring sphere 1710 and the second measuring sphere 1720 are viable options to measure the study subject (such as, e.g., a balloon that is inflated to six millimeters (mm) as in FIGS. 16A and 16B).

Figure 18:
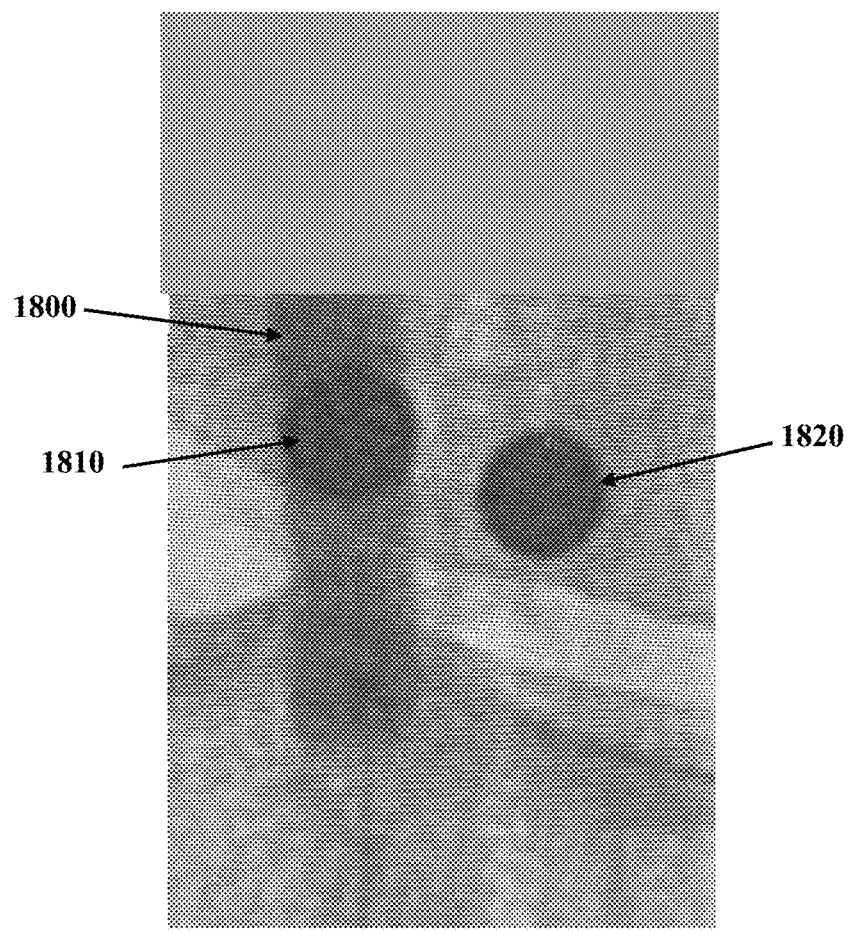
FIG. 18 is a photograph of an x-ray of a portion of a patient's leg having an inflatable balloon inserted into a vessel of the patient with a pair of spheres of a measuring device superimposed on to the vessel of the patient's leg according to one embodiment of the invention.

FIG. 18 is a photograph of an x-ray of a portion of a patient's leg having an inflatable balloon inserted into a vessel of the patient with a pair of spheres of a measuring device superimposed on to the vessel of the patient's leg according to one embodiment of the invention. As shown in FIG. 18, a balloon 1800, which is inserted into a vessel of a patient, is inflated to six millimeters (mm) at nominal pressure. A first measuring sphere 1810 is superimposed on to the inflated balloon 1800, while a second measuring sphere 1820 is located adjacent to the inflated balloon 1800 and the superimposed, first measuring sphere 1810. The first measuring sphere 1810 and the second measuring sphere 1820, which are both six millimeters (mm) in size, allow for accurately determining if the balloon 1800 has been inflated to the desired diameter (i.e., six millimeters (mm)).

FIGS. 19A-19E are photographs that illustrate a method of using a measuring device (or tape) having at least one measuring sphere to achieve an equivalent diameter between the sphere and an inflatable balloon inserted into a vessel of a patient according to an embodiment of the invention. As shown in FIG. 19A, a measuring device 1900 is provided that includes (i) a plurality of measurement marks 1940 for measuring a distance and/or a length of, for example, a vessel, and (ii) at least one circular indicator (or sphere) 1950 for measuring a diameter of, for example, a lumen of a vessel. In the embodiment of FIG. 19A, the circular indicator (or sphere) 1950 has a diameter of five millimeters (mm). In FIG. 19B, a balloon 1960, which is to be inflated to five millimeters (mm), has been inserted in a vessel of a patient and has been partially inflated. A portion of the balloon 1960 is fully inflated to five millimeters (mm) and has reached its compatible diameter, which is apparent by the circular indicator (or sphere) 1950 of the measuring device 1900, which has a diameter of five millimeters (mm), that has been superimposed on to this fully inflated portion of the balloon 1960. A second circular indicator (or sphere) 1955 on a second measuring device is positioned next to the circular indicator (or sphere) 1950 of the measuring device 1900 that has been superimposed on to this fully inflated portion of the balloon 1960. However, as shown in the image of FIG. 19B, a portion (I) of the balloon 1960 has not been fully inflated. In FIG. 19C, another circular indicator (or sphere) 1970 of another measuring device is superimposed onto the portion (I) of the balloon 1960 that has not been fully inflated. This circular indicator (or sphere) 1970 has a diameter of three millimeters (mm). Thus, as is apparent in the image of FIG. 19C, the portion (I) of the balloon 1960 that has not been fully inflated has only a diameter of three millimeters (mm) given that it is equivalent in size to the circular indicator (or sphere) 1970, which a diameter of three millimeters (mm), and is superimposed on to this portion (I) of the balloon 1960 that has not been fully inflated. Thus, the differential in the balloon diameter is determined by comparing both the circular indicator (or sphere) 1950 of the measuring device 1900, which has a diameter of five millimeters (mm), and the circular indicator (or sphere) 1970, which has a diameter of three millimeters (mm), to the various portions of the partially inflated balloon 1960. Therefore, additional pressure is required to change this portion (I) of the balloon 1960 that has not been fully inflated from three millimeters (mm) to the desired five millimeters (mm).

In FIG. 19D, an almost completely inflated balloon 1960 is shown by repositioning the circular indicator (or sphere) 1950 of the measuring device 1900 and the second circular indicator (or sphere) 1955 on to this portion (I) of the balloon 1960 that was previously only partially inflated. In this image of FIG. 19D, the second circular indicator (or sphere) 1955 is superimposed on to the portion (I) of the balloon 1960 that was previously only partially inflated. As shown in FIG. 19D, this portion (I) of the balloon 1960 is almost equivalent in size to the second circular indicator (or sphere) 1955 that is superimposed on to this portion (I) of the balloon 1960. Since the second circular indicator (or sphere) 1955 is a five millimeter (mm) sphere, it is apparent that this portion (I) of the balloon 1960 that was previously only partially inflated, is almost fully inflated, i.e., to five millimeters (mm) in diameter.

In FIG. 19E, a completely inflated balloon 1960 is shown by again positioning the circular indicator (or sphere) 1950 of the measuring device 1900 and the second circular indicator (or sphere) 1955 on to this portion (I) of the balloon 1960 that was previously only partially inflated. In this image of FIG. 19E, the circular indicator (or sphere) 1950 of the measuring device 1900 is superimposed on to the portion (I) of the balloon 1960 that was previously only partially inflated. As shown in FIG. 19E, this portion (I) of the balloon 1960 is now equivalent in size to the circular indicator (or sphere) 1950 of the measuring device 1900 that is superimposed on to this portion (I) of the balloon 1960. Since the circular indicator (or sphere) 1950 of the measuring device 1900 is a five millimeter (mm) sphere, it is apparent that this portion (I) of the balloon 1960 (i.e., the target area) that was previously only partially inflated, is completely inflated, i.e., to five millimeters (mm) in diameter. Thus, as shown in FIG. 19E, the final result has been achieved of completely inflating the balloon 1960 to its compatible diameter of five millimeters (mm). This final result has been easily visualized by the aid of the circular indicators (or spheres) (1950, 1955), which each have a diameter of five millimeters (mm), and a compared to the balloon 1960, which now has an equivalent diameter to these circular indicators (or spheres) (1950, 1955). Thus, according to the embodiment of FIGS. 19A-19E, the proper use of a measuring device of the invention is illustrated using a measuring device (or tape) 1900 and one or more circular indicators (or spheres) (1950, 1955) to thereby yield an equivalent diameter between the five millimeter (mm) circular indicators (or spheres) (1950, 1955) and the inflated balloon 1960.

Figure 20A:
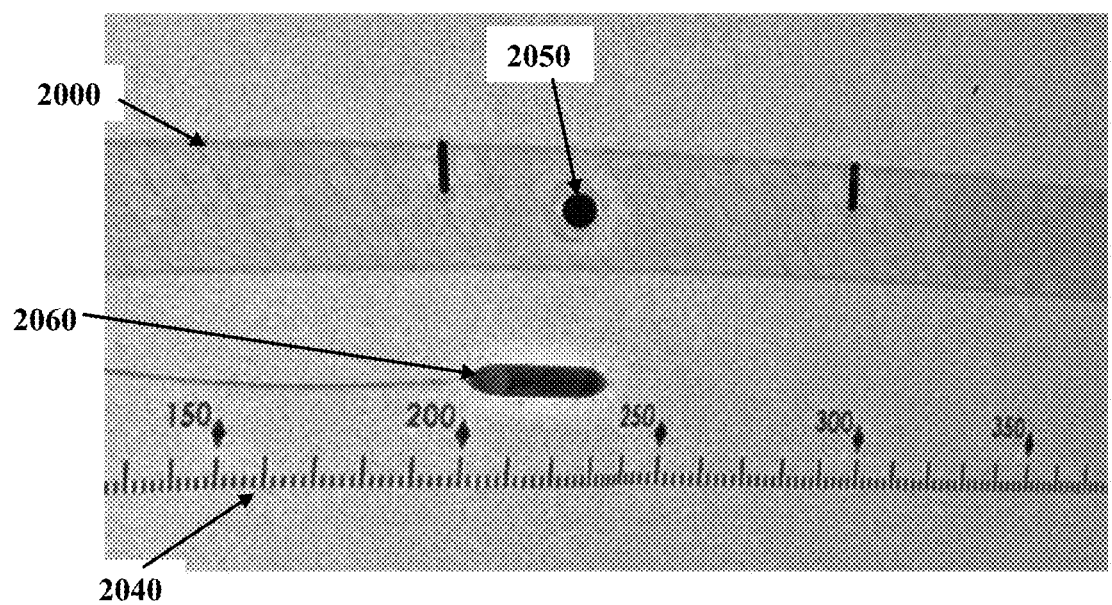
FIGS. 20A and 20B are photographs of an inflatable balloon in comparison to a measuring device having measurement marks and at least one circular indicator (or sphere) according to an embodiment of the invention.
Figure 20B:
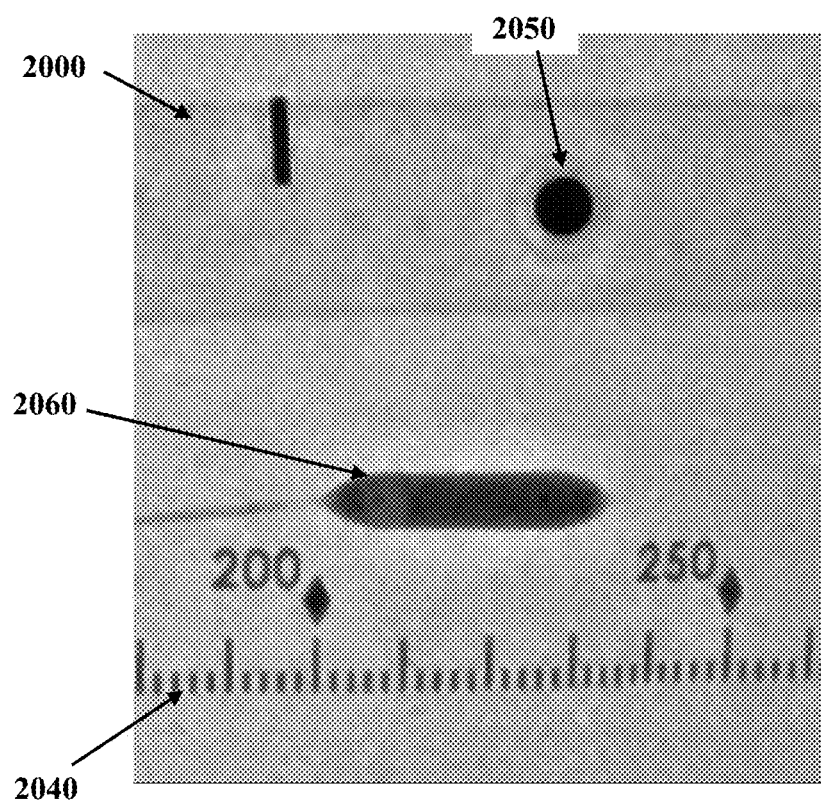

FIGS. 20A and 20B are photographs of an inflatable balloon in comparison to a measuring device having measurement marks and at least one circular indicator (or sphere) according to an embodiment of the invention. As shown in FIGS. 20A and 20B, a measuring device 2000 is provided that includes (i) a plurality of measurement marks 2040 for measuring a distance and/or a length of, for example, a vessel, and (ii) at least one circular indicator (or sphere) 2050 for measuring a diameter of, for example, a lumen of a vessel. Also shown in FIGS. 20A and 20B is an inflated balloon 2060, which has been inflated with contrast material and visualized under fluoroscopy. Thus, as shown in FIG. 20A (as well as FIG. 20B, which is an enlarged version of FIG. 20A), the circular indicator (or sphere) 2050, which is radiopaque, can be visualized under fluoroscopy and gives the same appearance as contrast color when seen by fluoroscopy. Accordingly, the contrast filled balloon 2060, which contains a contrast material, has the same or a very similar appearance to the circular indicator (or sphere) 2050, which does not contain contrast material, which allows for a comparison between the contrast filled balloon 2060 and the circular indicator (or sphere) 2050 very compatible and/or easily visualized.

Figure 21:
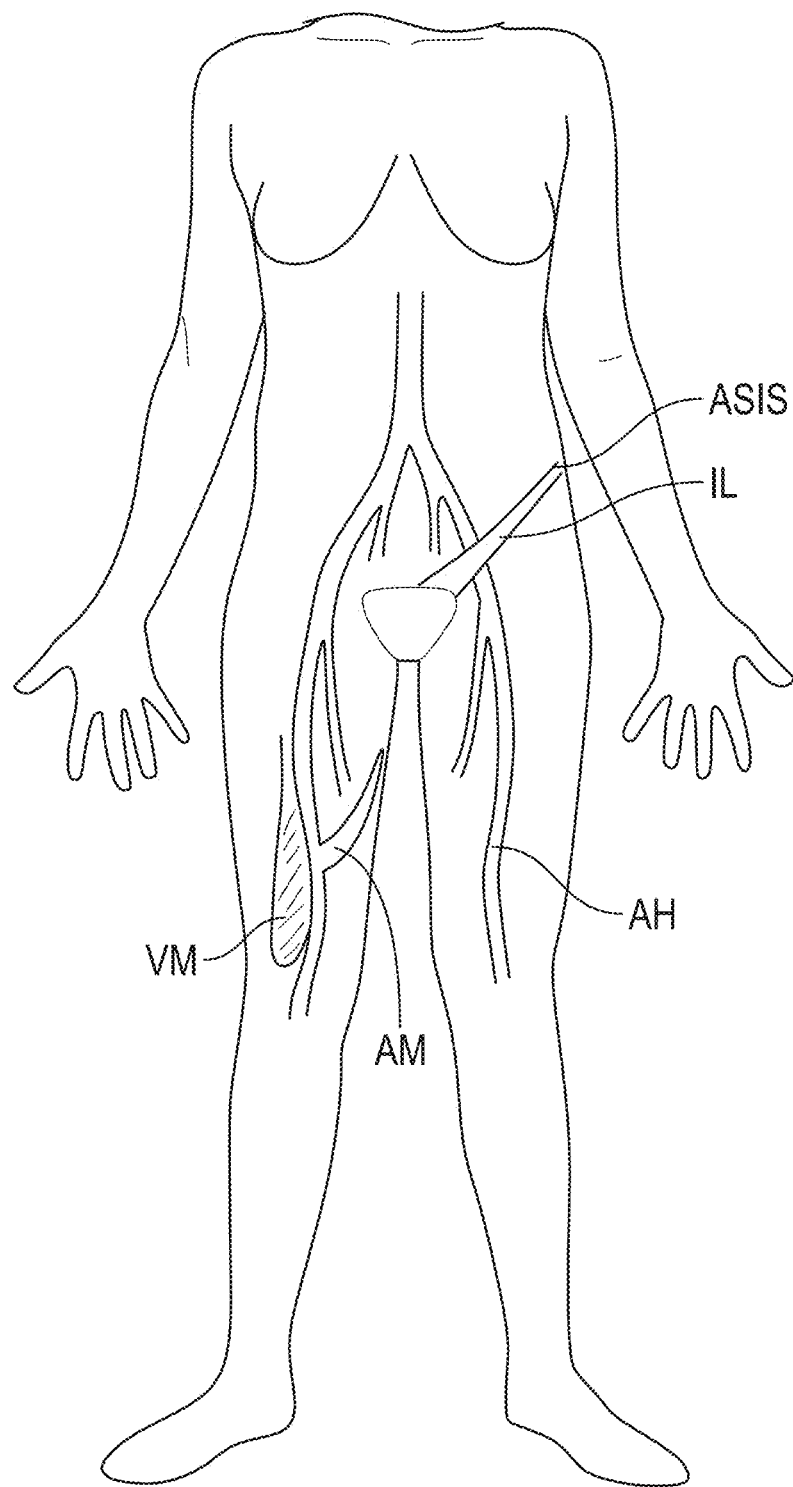
FIG. 21 illustrates an example of vessels of a human patient that can be measured by a measuring device according to an embodiment of the invention.

FIG. 21 illustrates an example of vessels of a human patient that can be measured by a measuring device according to an embodiment of the invention. For example, as shown in FIG. 21, a front portion of a human body is illustrated with the various vessels and their associated body parts of this front portion of the human body also being illustrated (i.e., the anterior superior iliac spine (ASIS), the inguinal ligament (IL), the adductor hiatus (AH), the adductor magnus (AM), and the vastus medialis (VM)). The various vessels of this front portion of a human body that is illustrated in FIG. 21 can be measured by positioning the measuring devices of the invention as described herein in various locations (see, e.g., FIGS. 22B and 22D). Thus, the measuring devices of the invention as described herein allow for measuring numerous different vessels of a human patient in a more efficient and accurate manner.

FIGS. 22A-22D are photographs that depict various measuring devices that can be placed on various body parts of a human patient according to embodiments of the invention. For example, as shown in FIG. 22A, a plurality of measuring devices (2200, 2210, 2220, 2230) are illustrated that can be positioned along the front upper leg, the front lower leg (or shin), the foot, and the back lower leg (or calf) of the human patient. In the embodiment of FIG. 22A, the measuring device 2220 positioned along the back lower leg (or calf) can include an indentation or groove that allows for it to be angled along the ankle and/or foot portion of the human patient.

In the embodiment of FIG. 22B, a first measuring device 2300 is illustrated that can be positioned in a spiral manner around the breast area of a human patient, while a second measuring device 2310 is illustrated that can be positioned along the arm of a human patient and a third measuring device 2320, which is in the form of a y-shaped measuring device 2320, is illustrated that can be positioned along a front portion of the human patient (see also, e.g., FIG. 21). In the embodiment of FIG. 22B, the first measuring device 2300, which can be positioned in a spiral manner around the breast area of a human patient, can include one or more circular indicators (or spheres) 2305 that allow for measuring, e.g., a vessel, a lumen, a lesion, and/or a mass within the breast area.

In the embodiment of FIG. 22C, a plurality of measuring devices (2400, 2410, 2420, 2430, 2440, 2450, 2460) are illustrated that can be positioned on various body parts of the human patient. For example, a first measuring device 2400 is illustrated that is positioned along a front area or abdominal region of the human patient. A second measuring device 2410 is illustrated that is positioned along an arm of the human patient. A third measuring device 2420 is illustrated that is positioned along a front upper leg portion (or thigh) of the human patient. A fourth measuring device 2430 is illustrated that is positioned along a front lower leg portion (or calf and knee) of the human patient. A fifth measuring device 2440 is illustrated that is positioned along a foot portion of the human patient. A sixth measuring device 2450 is illustrated that is positioned along a lower side leg portion (or calf) to the knee of the human patient. A seventh measuring device 2460 is illustrated that is positioned along a knee and an upper leg portion (or thigh) of the human patient. In the embodiment of FIG. 22D, a first measuring device 2500 is positioned along an arm of the human patient, while a second measuring device 2510, which is a y-shaped measuring device 2510 having an upper loop portion, is positioned along a chest area and an abdominal region of the human patient, and a third measuring device 2520 is positioned along a front upper leg portion (or thigh) of the human patient. Thus, as shown in FIGS. 22A-22D, a plurality of measurement devices of the invention as described herein can be positioned on to numerous regions and/or areas of the human patient and in various configurations in order to measure, e.g., certain vessels, lumens, lesions, and/or masses that are necessary for certain medical procedures.

Although the embodiments described above disclose and illustrate the positioning of the measuring device(s) on various leg and/or foot portions of a patient, the measuring device(s) can be positioned on all extremities (e.g., arms and legs) and any area of the body where (i) a vessel is to be treated, including, e.g., with a balloon for expansion of the vessel, and/or (ii) arteries and/or veins are provided, and in which a vessel/lesion/lumen/mass length measurement is required and/or a vessel/lumen/mass diameter measurement is required. For example, the measuring device(s) can be positioned on the neck (e.g., carotid arteries) and/or the torso (e.g., renal arteries, mesenteric arteries, aortic artery, iliac arteries and the entire venous system).

In accordance with the principles of the invention, a unique measuring device with one or more measuring tapes is provided that can be used to simultaneously evaluate multiple circulatory distributions of various arteries, including, e.g., the tibial pedal arteries, which is usually referred to as anterior and posterior circulations as well as plantar and dorsal circulation. Moreover, according to aspects of the invention, a measuring device having one or more measuring tapes is provided that helps to measure and to diagnose various lesion locations and/or diameters, including, e.g., the pedal loop.

In accordance with the principles of the invention, a unique measuring device is provided that provides both (i) rigidity and strength that allows for substantially straight and extremely accurate measurements of distances and/or lengths of various body parts, including, e.g., vessels, and (ii) flexibility that allows for bending and/or curving of the device to accommodate the various curves and variations of the body. Moreover, according to an embodiment, the unique measuring device includes rigidity, strength, and flexibility, while eliminating the foreshortening of previous measurement tapes or devices known in the art.

Further aspects of the present disclosure are provided by the subject matter of the following clauses.

A measuring device comprising one or more measurement tapes having (i) a plurality of measurement marks for measuring a distance and/or a length of a vessel and (ii) a plurality of circular indicators for measuring a diameter of a lumen of the vessel.

The measuring device of any preceding clause, wherein each measurement mark of the plurality of measurement marks is positioned the same distance from an adjacent measurement mark of the plurality of measurement marks.

The measuring device of any preceding clause, wherein each measurement mark of the plurality of measurement marks is positioned 5 centimeters from an adjacent measurement mark of the plurality of measurement marks.

The measuring device of any preceding clause, wherein each measurement mark of the plurality of measurement marks is positioned 1 centimeter from an adjacent measurement mark of the plurality of measurement marks.

The measuring device of any preceding clause, wherein each measurement mark of the plurality of measurement marks comprises a number.

The measuring device of any preceding clause, wherein a plurality of sub-markers is positioned between each measurement mark of the plurality of measurement marks.

The measuring device of any preceding clause, wherein each sub-marker of the plurality of sub-markers is positioned the same distance from an adjacent sub-marker of the plurality of sub-markers.

The measuring device of any preceding clause, wherein each sub-marker of the plurality of sub-markers is positioned 1 centimeter from an adjacent sub-marker of the plurality of sub-markers.

The measuring device of any preceding clause, wherein the measuring device comprises at least two measurement tapes that comprise mirror images of each other.

The measuring device of any preceding clause, wherein the measuring device comprises at least two measurement tapes that are positioned parallel to each other.

The measuring device of any preceding clause, wherein the measuring device comprises at least two measurement tapes that are connected via one or more straps.

The measuring device of any preceding clause, wherein the one or more straps further comprise a plurality of measurement marks.

The measuring device of any preceding clause, wherein the measuring device comprises at least two measurement tapes in the form of a y-shape with (i) the at least two measurement tapes being positioned parallel to each other along a first length, and (ii) the at least two measurement tapes diverging at an angle with respect to each other along a second length to form the y-shape.

The measuring device of any preceding clause, wherein the measuring device comprises at least one measurement tape having (i) a first portion that is straight and (ii) a second portion that is at an angle relative to the first portion.

The measuring device of any preceding clause, wherein the measuring device further includes an indicator portion that is configured to enhance an angulation of the measuring device.

The measuring device of any preceding clause, wherein the measuring device comprises at least one measurement tape that is 70 cm in length.

The measuring device of any preceding clause, wherein the plurality of circular indicators for measuring a diameter of a lumen are differing sizes from each other.

The measuring device of any preceding clause, wherein the plurality of circular indicators comprise differing sizes that include two or more of (i) a 2 mm diameter circle, (ii) a 2.5 mm diameter circle, (iii) a 3 mm diameter circle, (iv) a 3.5 mm diameter circle, (v) a 4 mm diameter circle, (vi) a 5 mm diameter circle, (vii) a 5.5 mm diameter circle, (viii) a 6 mm diameter circle, (ix) a 6.5 mm diameter circle, (x) a 7 mm diameter circle, and (xi) an 8 mm diameter circle.

The measuring device of any preceding clause, wherein the plurality of circular indicators for measuring a diameter of a lumen comprise radiopaque markers.

A method of measuring at least one of (i) a distance and/or a length of a vessel and (ii) a diameter of a lumen of a vessel that includes (a) providing a measuring device comprising one or more measurement tapes having (i) a plurality of measurement marks for measuring the distance and/or the length of the vessel and (ii) a plurality of circular indicators for measuring the diameter of the lumen of the vessel, (b) positioning the measuring device on a body part of a patient, and (c) measuring the at least one of (i) a distance and/or a length of the vessel and (ii) a diameter of a lumen of the vessel.

The method of any preceding clause, wherein the measuring device comprises at least one measurement tape, and the method includes positioning the at least one measurement tape along a thigh of a patient to measure a vessel within the thigh of the patient.

The method of any preceding clause, wherein the measuring device comprises at least two measurement tapes, and the method includes positioning (i) a first measurement tape of the at least two measurement tapes along a calf of a patient, and (ii) a second measurement tape of the at least two measurement tapes along a shin of a patient.

The method of any preceding clause, wherein the method further includes positioning (i) a portion of the first measurement tape of the at least two measurement tapes along a bottom or plantar portion of a foot of the patient, and (ii) a portion of the second measurement tape of the at least two measurement tapes along a top or dorsal portion of the foot of the patient.

A measuring device comprising at least one measurement tape having (i) a plurality of measurement marks for measuring a distance and/or a length of a vessel and (ii) a plurality of cylindrical elements that each house a measuring sphere for measuring a diameter of a lumen of the vessel.

The measuring device of any preceding clause, wherein each measuring sphere is embedded within a respective cylindrical element of the plurality of cylindrical elements via a filling material.

The measuring device of any preceding clause, wherein each measuring sphere housed within a respective cylindrical element of the plurality of cylindrical elements decreases in size from a distal end to a proximal end of the measuring device.

The measuring device of any preceding clause, wherein the measuring device further comprises one or more indentations disposed along the at least one measurement tape that allow for folding of the measuring device.

The measuring device of any preceding clause, wherein each cylindrical element of the plurality of cylindrical elements is positioned a certain distance from another cylindrical element of the plurality of cylindrical elements.

The measuring device of any preceding clause, wherein each cylindrical element of the plurality of cylindrical elements is positioned a distance of 50 mm to 100 mm from another cylindrical element of the plurality of cylindrical elements.

The measuring device of any preceding clause, wherein each cylindrical element of the plurality of cylindrical elements is positioned a distance of 50 mm to 75 mm from another cylindrical element of the plurality of cylindrical elements.

The measuring device of any preceding clause, wherein the measuring device further comprises one or more hinge members to allow for the measuring device to be folded during shipping and/or storage.

A measuring device comprising at least one measurement tape having at least one measuring sphere, wherein the at least one measuring sphere comprises a radiopaque material that allows for visualizing the at least one measuring sphere under x-ray at any angle.

The measuring device of any preceding clause, wherein the at least one measuring sphere is configured to measure at least one of (i) a vessel, (ii) a lumen, (iii) a mass, (iv) an inserted balloon, or (v) a combination of (i), (ii), (iii), or (iv).

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A measuring device comprising one or more measurement tapes having (i) a plurality of measurement marks for measuring one or more of a distance and a length of a vessel and (ii) a plurality of circular indicators for measuring a diameter of a lumen of the vessel,
   wherein the plurality of circular indicators for measuring a diameter of a lumen comprise radiopaque markers.

2. The measuring device according to claim 1, wherein each measurement mark of the plurality of measurement marks is positioned the same distance from an adjacent measurement mark of the plurality of measurement marks.

3. The measuring device according to claim 2, wherein each measurement mark of the plurality of measurement marks is positioned 5 centimeters from an adjacent measurement mark of the plurality of measurement marks.

4. The measuring device according to claim 2, wherein each measurement mark of the plurality of measurement marks is positioned 1 centimeter from an adjacent measurement mark of the plurality of measurement marks.

5. The measuring device according to claim 1, wherein each measurement mark of the plurality of measurement marks comprises a number.

6. The measuring device according to claim 1, further comprising a plurality of sub-markers positioned between each measurement mark of the plurality of measurement marks.

7. The measuring device according to claim 6, wherein each sub-marker of the plurality of sub-markers is positioned the same distance from an adjacent sub-marker of the plurality of sub-markers.

8. The measuring device according to claim 7, wherein each sub-marker of the plurality of sub-markers is positioned 1 centimeter from an adjacent sub-marker of the plurality of sub-markers.

9. The measuring device according to claim 1, wherein the measurement device comprises at least two measurement tapes that comprise mirror images of each other.

10. The measuring device according to claim 1, wherein the measurement device comprises at least two measurement tapes that are positioned parallel to each other.

11. The measuring device according to claim 1, wherein the measurement device comprises at least two measurement tapes that are connected via one or more straps.

12. The measuring device according to claim 11, wherein the one or more straps further comprise a plurality of measurement marks.

13. The measuring device according to claim 1, wherein the plurality of circular indicators for measuring a diameter of a lumen are differing sizes from each other.

14. The measuring device according to claim 13, wherein the plurality of circular indicators comprise differing sizes that include two or more of (i) a 2 mm diameter circle, (ii) a 2.5 mm diameter circle, (iii) a 3 mm diameter circle, (iv) a 3.5 mm diameter circle, (v) a 4 mm diameter circle, (vi) a 5 mm diameter circle, (vii) a 5.5 mm diameter circle, (viii) a 6 mm diameter circle, (ix) a 6.5 mm diameter circle, (x) a 7 mm diameter circle, and (xi) an 8 mm diameter circle.

15. The measuring device according to claim 1, wherein the measuring device comprises at least two measurement tapes in the form of a y-shape with (i) the at least two measurement tapes being positioned parallel to each other along a first length, and (ii) the at least two measurement tapes diverging at an angle with respect to each other along a second length to form the y-shape.

16. The measuring device according to claim 1, wherein the measuring device comprises at least one measurement tape having (i) a first portion that is straight and (ii) a second portion that is at an angle relative to the first portion.

17. The measuring device according to claim 16, wherein the measuring device further includes an indicator portion that is configured to enhance an angulation of the measuring device.

18. The measuring device according to claim 1, wherein the measuring device comprises at least one measurement tape that is 70 cm in length.

19. The measuring device according to claim 1, wherein each circular indicator of the plurality of circular indicators comprises a sphere.

20. A method of measuring at least one of (i) one or more of a distance and a length of a vessel or (ii) a diameter of a lumen of a vessel, the method comprising:
   (a) providing a measuring device comprising one or more measurement tapes having (i) a plurality of measurement marks for measuring the one or more of a distance and a length of the vessel and (ii) a plurality of circular indicators for measuring the diameter of the lumen of the vessel;
   (b) positioning the measuring device on a body part of a patient; and (c) measuring the at least one of (i) one or more of a distance and a length of the vessel or (ii) a diameter of a lumen of the vessel.

21. The method according to claim 20, wherein the measuring device comprises at least one measurement tape, and the method includes positioning the at least one measurement tape along a thigh of a patient to measure a vessel within the thigh of the patient.

22. The method according to claim 20, wherein the measuring device comprises at least two measurement tapes, and the method includes positioning (i) a first measurement tape of the at least two measurement tapes along a calf of a patient, and (ii) a second measurement tape of the at least two measurement tapes along a shin of a patient.

23. The method according to claim 22, wherein the method further includes positioning (i) a portion of the first measurement tape of the at least two measurement tapes along a bottom or plantar portion of a foot of the patient, and (ii) a portion of the second measurement tape of the at least two measurement tapes along a top or dorsal portion of the foot of the patient.

24. The method according to claim 20, wherein each circular indicator of the plurality of circular indicators comprises a sphere.

25. A measuring device comprising at least one measurement tape having (i) a plurality of measurement marks for measuring one or more of a distance and a length of a vessel and (ii) a plurality of cylindrical elements that each house a measuring sphere for measuring a diameter of a lumen of the vessel.

26. The measuring device according to claim 25, wherein each measuring sphere is embedded within a respective cylindrical element of the plurality of cylindrical elements via a filling material.

27. The measuring device according to claim 25, wherein each measuring sphere housed within a respective cylindrical element of the plurality of cylindrical elements decreases in size from a distal end to a proximal end of the measuring device.

28. The measuring device according to claim 25, wherein the measuring device further comprises one or more indentations disposed along the at least one measurement tape that allow for folding of the measuring device.

29. The measuring device according to claim 25, wherein each cylindrical element of the plurality of cylindrical elements is positioned a certain distance from another cylindrical element of the plurality of cylindrical elements.

30. The measuring device according to claim 29, wherein each cylindrical element of the plurality of cylindrical elements is positioned a distance of 50 mm to 100 mm from another cylindrical element of the plurality of cylindrical elements.

31. The measuring device according to claim 29, wherein each cylindrical element of the plurality of cylindrical elements is positioned a distance of 50 mm to 75 mm from another cylindrical element of the plurality of cylindrical elements.

32. The measuring device according to claim 25, wherein the measuring device further comprises one or more connection members to allow for the measuring device to be folded during at least one of shipping and storage.

33. A measuring device comprising at least one measurement tape having at least one measuring sphere, wherein the at least one measuring sphere comprises a radiopaque material that allows for visualizing the at least one measuring sphere under x-ray at any angle.

34. The measuring device according to claim 33, wherein the at least one measuring sphere is configured to measure at least one of (i) a vessel, (ii) a lumen, (iii) a mass, (iv) an inserted balloon, or (v) a combination of (i), (ii), (iii), or (iv).

\* \* \* \* \*